(12) United States Patent
Caprioli et al.

(10) Patent No.: US 10,996,227 B2
(45) Date of Patent: May 4, 2021

(54) PRE-COATED SURFACES FOR IMAGING BIOMOLECULES

(71) Applicant: Vanderbilt University, Nashville, TN (US)

(72) Inventors: Richard Caprioli, Brentwood, TN (US); Junhai Yang, Nashville, TN (US); Jeremy L. Norris, Smyrna, TN (US); Faizan Zubair, Nashville, TN (US); Paul Edward Laibinis, Brentwood, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 648 days.

(21) Appl. No.: 15/177,819

(22) Filed: Jun. 9, 2016

(65) Prior Publication Data

US 2017/0067906 A1    Mar. 9, 2017

Related U.S. Application Data

(60) Provisional application No. 62/172,960, filed on Jun. 9, 2015.

(51) Int. Cl.
| | |
|---|---|
| *G01N 30/72* | (2006.01) |
| *G01N 33/68* | (2006.01) |
| *G01N 23/2258* | (2018.01) |
| *A61K 38/00* | (2006.01) |

(52) U.S. Cl.
CPC ..... *G01N 33/6851* (2013.01); *G01N 23/2258* (2013.01)

(58) Field of Classification Search
CPC ............... G01N 23/2258; G01N 33/68; G01N 33/4833; G01N 2333/95
See application file for complete search history.

(56) References Cited

U.S. PATENT DOCUMENTS

| | | | |
|---|---|---|---|
| 2005/0277125 A1* | 12/2005 | Benn .................... | B01J 19/0046 435/6.11 |
| 2012/0109530 A1* | 5/2012 | Parks ...................... | G06F 19/24 702/19 |

FOREIGN PATENT DOCUMENTS

WO    WO-03078452 A1 *  9/2003   ......... G01N 33/6848

OTHER PUBLICATIONS

Rohner et al. (200%) MALDI mass spectrometric imaging of biological tissue sections, Mechanism. Ageing Dev., vol. 126, pp. 177-185.*
Lim et al. (2014) Correlated matrix-assisted laser desorption/ionization mass spectrometry and fluorescent imaging of photocleavable peptide-coded random bead-arrays, Rapid Commum. Mass Spectrom., vol. 28, pp. 49-62.*
Chughtai et al. (2010) Mass Spectrometric Imaging for biomedical tissue analysis, Chem. Rev., vol. 110, No. 5, pp. 3237-3277.*
Switzar et al. (2013) Protein Digestion: An Overview of the Available Techniques and Recent Developments, J. Proteome Res., vol. 12, pp. 1067-1077.*
Norris et al. (2013) Analysis of Tissue Specimens by Matrix-Assisted Laser Desorption/ionization Imaging Mass Spectrometry in Biological and Clinical Research, Chem Rev., vol. 113, pp. 2309-2342.*

* cited by examiner

*Primary Examiner* — Manjunath N Rao
*Assistant Examiner* — Samuel W Liu
(74) *Attorney, Agent, or Firm* — Tarolli, Sundheim, Covell & Tummino LLP

(57) ABSTRACT

Pre-coated analysis substrates, and methods of making the substrates and using them to analyze animal tissue, are described. The pre-coated analysis substrates can be made by forming a matrix surface on an analysis substrate; adding a protease to the matrix surface to form a pre-coated analysis substrate; and placing an animal tissue specimen on the matrix surface. The animal tissue can then be analyzed by allowing the protease to partially digest the animal tissue specimen; and analyzing the partially digested animal tissue specimen by mass spectrometry.

26 Claims, 17 Drawing Sheets

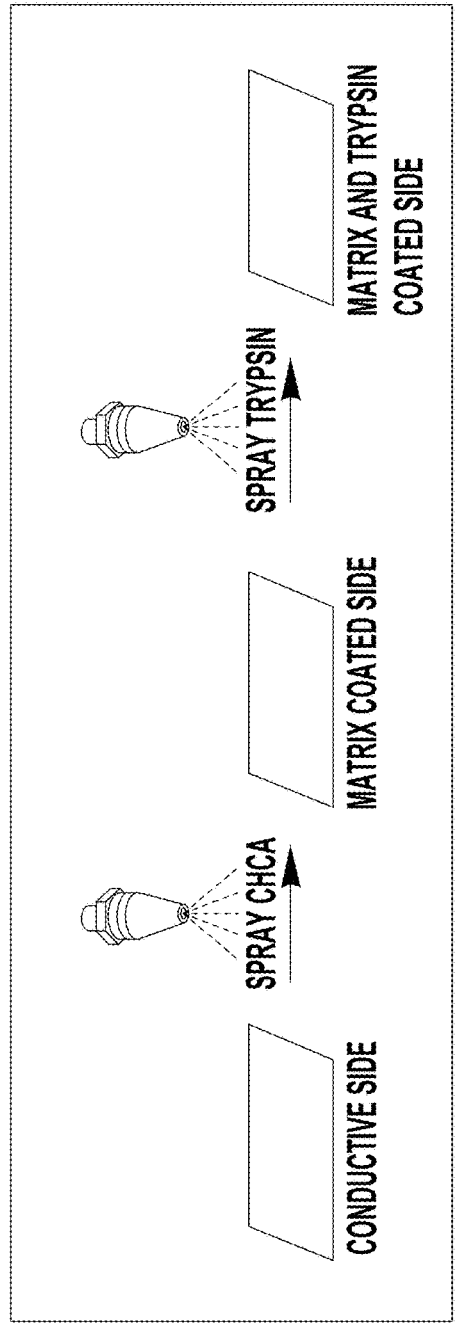
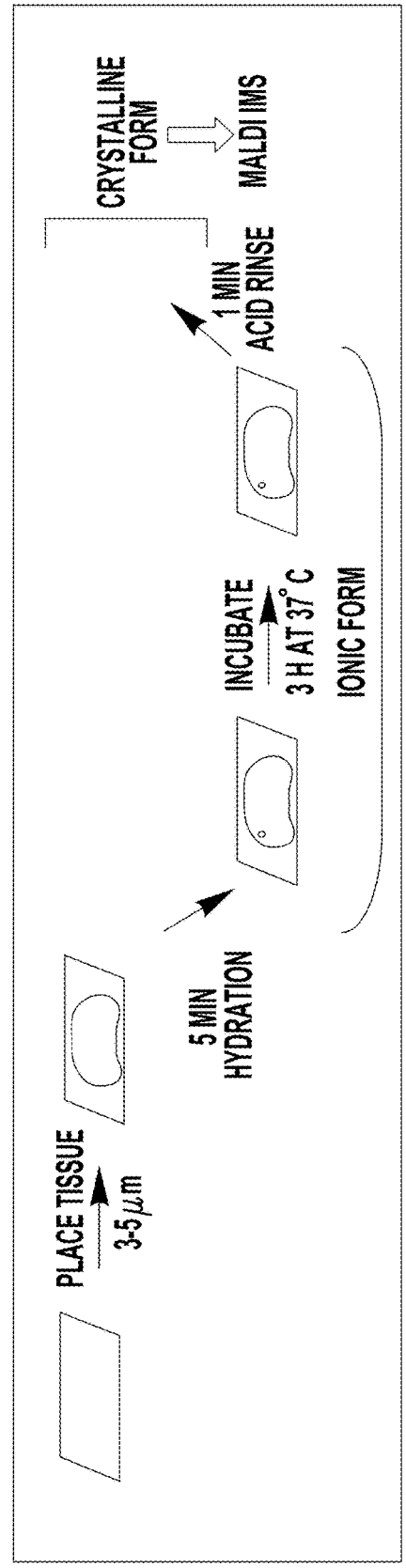
FIG. 3A
FIG. 3B

DRY INCUBATION CHAMBER

WET INCUBATION CHAMBER

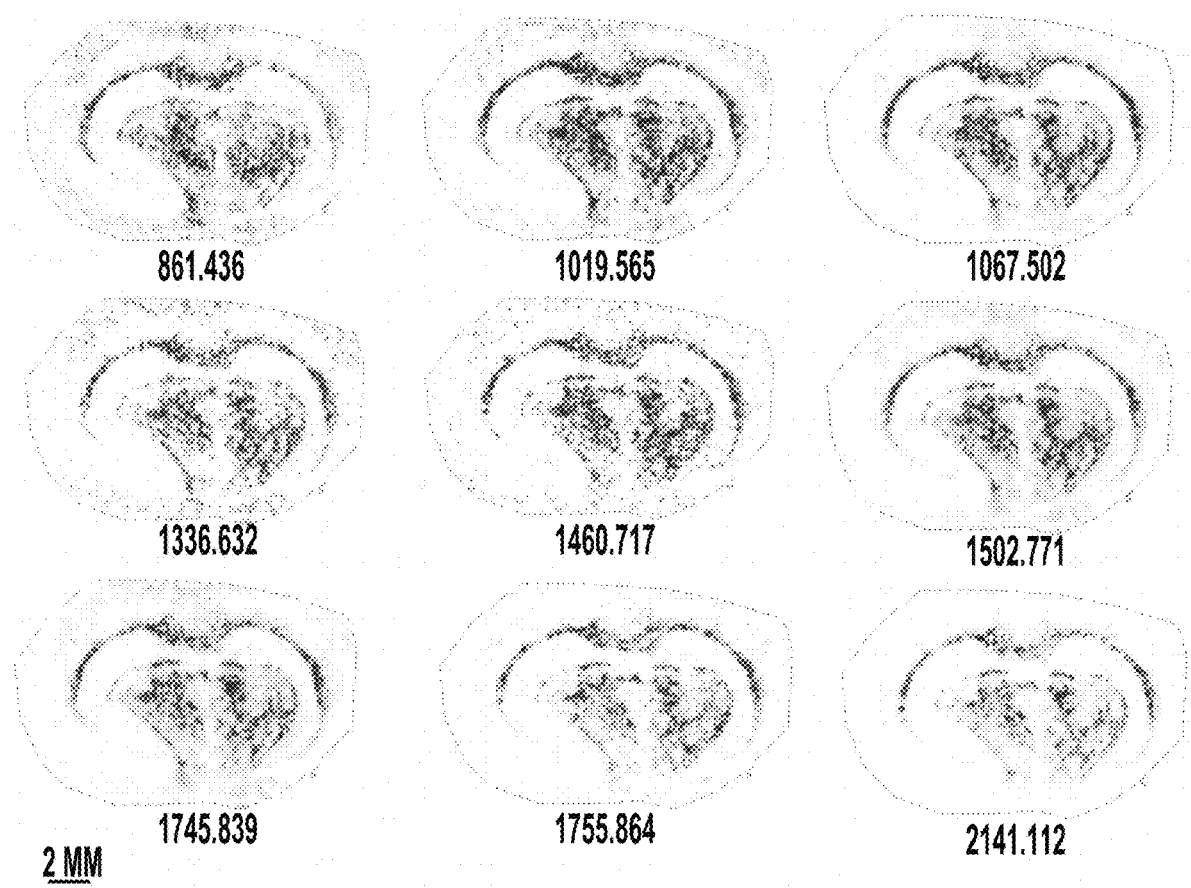

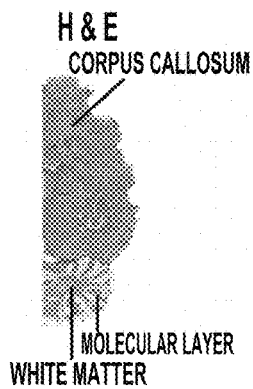
H & E
CORPUS CALLOSUM
MOLECULAR LAYER
WHITE MATTER
FIG. 14A
1502.774    1745.841    2141.110    2933.519
MYELIN BASIC PROTEIN
FIG. 14B
1192.613    1781.843    1904.895
NEUROGRANIN
FIG. 14C
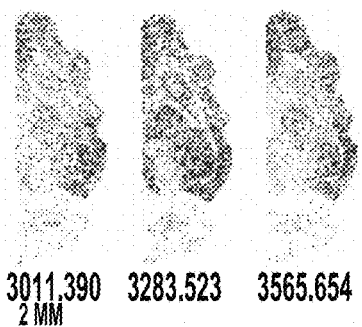
BRAIN ACID SOLUBLE PROTEIN 1
3011.390    3283.523    3565.654
2 MM
FIG. 14D
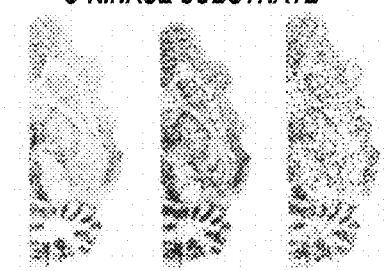
MYRISTOYLATED ALANINE-RICH C-KINASE SUBSTRATE
2432.094    2799.2116    3558.608
FIG. 14E
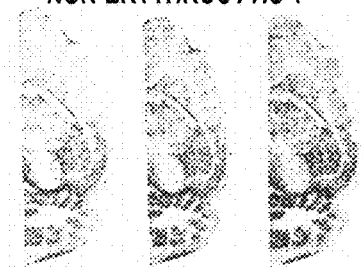
SPECTRIN ALPHA CHAIN, NON-ERYTHROCYTIC 1
1676.782    1774.849    2271.148
FIG. 14F
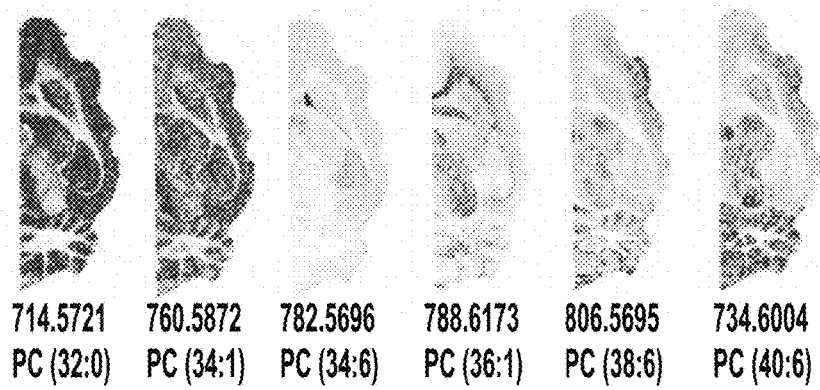
714.5721    760.5872    782.5696    788.6173    806.5695    734.6004
PC (32:0)   PC (34:1)   PC (34:6)   PC (36:1)   PC (38:6)   PC (40:6)
FIG. 15

FRESHLY PREPARED SLIDES 1502.773   1745.839   2141.107   2935.279

6 MONTHS 1502.773   1745.839   2141.107   2935.279

18 MONTHS 1502.773   1745.839   2141.107   2935.279

PRE-COATED SURFACES FOR IMAGING BIOMOLECULES

CONTINUING APPLICATION DATA

This application claims the benefit of U.S. Provisional Application Ser. No. 62/172,960, filed Jun. 9, 2015, the disclosure of which is incorporated by reference herein.

STATEMENT REGARDING FEDERALLY SPONSORED RESEARCH

This invention was made with government support under grant 5P41 GM103391-03 awarded by the National Institutes of Health. The Government has certain rights in this invention.

BACKGROUND

The preparation of tissue samples is of primary importance to the nature and quality of information obtained using Imaging Mass Spectrometry (IMS). Unlike other analytical applications of mass spectrometry, where sensitivity and molecular specificity are the primary considerations for developing and validating methodologies, imaging applications require additional attention to preserve the spatial information in the sample. Furthermore, to promote adoption of the technology for significant translational applications targeting human health and disease, the ease-of-use of sample preparation methods must be optimized to ensure robust application of the technology by scientists and technicians whose primary training is in disciplines other than analytical chemistry.

Matrix-assisted laser desorption/ionization imaging mass spectrometry (MALDI-IMS) is a powerful technology in biological research enabling imaging of biomolecules within thin tissue specimens. In a typical experiment, a thin tissue (3-12 μm) is cryosectioned and placed on a conductive substrate. The tissue section is washed to remove salts and unwanted species, and then coated with a MALDI matrix that is typically a small organic molecule. The matrix aids in the desorption and ionization of the analytes. Analysis is performed by scanning a laser across the tissue section, acquiring mass spectral data at each defined x, y position. Two-dimensional maps of molecular distributions are generated from the spectral intensity for ions of interest across the sample.

In a typical MALDI imaging experiment, signals from proteins up to 25 kDa in molecular weight can be obtained directly from a tissue sample. Larger proteins are difficult to detect as the detection efficiency of a microchannel plate detector declines as the mass of the ion increases. Gilmore et al., Int. J. Mass Spectrom. 202, 217-229 (2000). Additionally, larger proteins are difficult to solubilize and incorporate into the matrix crystals. Franck et al., Med. Sci. Monitor 16 (2010), 293-299. This limitation precludes the observation of higher molecular weight biological species such as cytokines, growth factors, enzymes, receptors, and other biomolecules. Specific sample preparation methods have been developed to detect proteins up to 70 kDa in mass. These include the application of ferulic acid as a matrix and use of Triton X-100 and xylene to solubilize large proteins. Mainini et al., Mol Biosyst. 9 1101-1107 (2013); Leinweber et al., J. Am. Soc. Mass Spectr. 20, 89-96 (2009). Due to inherent limitations in detection and ion optics, such large proteins are difficult to detect on a routine basis. Chen et al., Anal. Chem. 75, 5944-5952 (2003).

An approach for measuring the distribution of large proteins (>25 kDa) in a tissue sample by MALDI-IMS involves their in situ tryptic digestion and subsequent MS imaging of generated fragments has been described. Groseclose et al., J. Mass Spectrom. 42, 254-262 (2007). In this approach, trypsin is serially spotted onto a tissue section to digest the proteins. Robotic spotters are used to control the digestion conditions, and in a second step, spot matrix on top of these individual regions. These post-coating methods have been used for the analysis of both formalin-fixed and fresh-frozen tissues. Groseclose et al., Proteomics 8, 3715-3724 (2008); Casadonte, R., and Caprioli, R. M., Nat. Protoc. 6, 1695-1709 (2011); Groseclose et al., J. Mass Spectrom. 42, 254-262 (2007). The advantages of this in situ digestion process include an on-tissue identification of proteins and a preservation of their spatial localization in contrast to LC-MS/MS approaches that are done on tissue homogenates where spatial information is limited. Further, the on-tissue analysis provides spatial distributions for the parent proteins and their daughter peptides that can be co-related and provide further verification in the identification. Despite these advantages, its use is challenged by a cumbersome process whereby sequentially spotting of matrix and trypsin onto a tissue sample can take hours for each tissue specimen. In addition, the robotic spotters needed for trypsin deposition are costly, and their spatial resolution is limited to 200-300 μm.

Previous work by the inventors has shown that matrix pre-coated targets can provide simple, standardized, and rapid methods for sample preparation. One group used pre-coated targets consisted of thin matrix films for the imaging of small molecules across a series of tissue sections. Grove et al., J. Am. Soc. Mass Spectr. 22, 192-195 (2011). Another group successfully demonstrated lipid imaging and protein distributions in brain and kidney tissues using such pre-coated slides. Yang, J. H. and Caprioli, R. M., Anal. Chem. 85 2907-2912 (2013); Yang, J. H. and Caprioli, R. M., J. Mass Spectrom. 49, 417-422 (2014). However, the need remains for improved methods of conducting Imaging Mass Spectrometry.

SUMMARY

As an alternative to current post-tissue processing, methods for MALDI-IMS have been developed that incorporate species such as matrix and enzymes onto targets prior to tissue availability. The goal is to simplify tissue preparation for MALDI-IMS and avoid time-consuming post-tissue deposition steps and the need for costly specialized equipment. Herein, the development of targets pre-coated with both an enzyme and matrix and their use for the indirect imaging of large proteins from generated tryptic fragments on frozen tissue samples is described. A major accomplishment of this work was the fabrication of trypsin pre-coated substrates for high-throughput proteomic analysis. Trypsin and matrix were spray-coated onto ITO-coated slides, and a tissue was thaw-mounted onto these pre-coated slides. The peptides can be digested, imaged and identified based on mass accuracy. These targets streamline the process for preparing tissue samples, minimize the burden of sample preparation on the end user and improve spatial resolution from 200 μm to 75 μm.

In one aspect the present invention provides a method for analyzing animal tissue that includes the steps of forming a matrix surface on an analysis substrate; adding a protease to the matrix surface to form a pre-coated analysis substrate; placing an animal tissue specimen on the matrix surface;

allowing the protease to partially digest the animal tissue specimen; and analyzing the partially digested animal tissue specimen by mass spectrometry. The animal tissue can be analyzed for the presence of one or more biomolecules. In some embodiments, the digested animal tissue specimen is evaluated for peptides, while in other embodiments, the digested animal tissue is evaluated for lipids.

Alternately, in another aspect, the present invention provides a method for analyzing animal tissue that does not use a matrix. This method includes the steps of coating a protease on a surface of an analysis substrate to form a pre-coated analysis substrate; placing an animal tissue specimen on the protease coated surface; allowing the protease to partially digest the animal tissue specimen; and analyzing the partially digested animal tissue specimen by mass spectrometry.

Another aspect of the invention provides a method of preparing a pre-coated analysis substrate that includes the steps of forming a matrix surface on an analysis substrate; adding a protease to the matrix surface to form a pre-coated analysis substrate; and storing the pre-coated analysis substrate for 24 hours or more before use. In this aspect of the method, the pre-coated analysis substrate is not used immediately, but is rather stored for later use. This aspect of the method reflects the discovery that the pre-coated analysis substrates are stable for a substantial period of time, and therefore can be prepared in batches ahead of time to allow for more efficient production and use.

Likewise, another aspect of the invention is directed to the use of a pre-coated analysis substrate that has been previously prepared. In this aspect, the invention provides a method for analyzing animal tissue using a pre-coated analysis substrate that includes the steps of placing an animal tissue specimen on a matrix surface comprising a protease on an analysis substrate; allowing the protease to partially digest the animal tissue specimen; and analyzing the partially digested animal tissue specimen by mass spectrometry Another aspect of the invention is directed to a pre-coated analysis substrate. The pre-coated analysis substrate includes an analysis substrate, upon which is placed a matrix including a protease, or protease alone. The pre-coated analysis substrate can be used immediately for carrying out an analysis of animal tissue using mass spectrometry, or it can be stored and used later.

BRIEF DESCRIPTION OF THE FIGURES

FIGS. 3A and 3B provide schemes showing (a) the sequential matrix and trypsin spray application onto a conductive substrate and (b) the general procedure for preparing a tissue sample for analysis using a pre-coated slide. The tissue sample is placed onto a pre-coated slide. It is hydrated by exposure to N,N-diisopropylethylamine (DIEA) and water and then incubated in a sealed chamber for 3 to 16 h at 37° C. Immersion in 10% TFA for 1 min returns the matrix to its crystalline form.

FIG. 9(a) was obtained from a digestion conducted in a dry incubation chamber, while FIG. 9(b) was a digest conducted in a wet incubation chamber.

FIG. 10(a) shows clear localization in dry samples, which is contrasted by delocalization observed in FIG. 10(b).

FIG. 12 provides ion images for tryptic fragments of 14.2 kDa isoform of myelin basic protein. Rat brain tissue section was prepared using pre-coated approach and the data were acquired using 15 T MALDI-Fourier transform ion cyclotron resonance (FTICR) instrument. The images were acquired at 100 µm spatial resolution. All nine signals were matched to theoretical masses within 1 ppm.

FIGS. 13A and 13B provide images of tryptic fragments of rat brain tissue sections and (a) Neurogranin (7.5 kDa) and (b) PEP-19 (6.8 kDa). Neurogranin is localized in the cerebral cortex and hippocampal region of the brain. PEP-19 is localized in the thalamus and the cerebral cortex.

FIGS. 14A-14F provide MALDI ion images of horizontal rat brain tissue section. FIG. 14(a) is a serial section stained using hematoxylin and eosin (H&E). Peptides corresponding to (b) Myelin basic protein (c) Neurogranin (d) Brain acid soluble protein 1 (e) Myristoylated alanine-rich C-kinase substrate (f) Spectrin alpha chain, non-erythrocytic 1 are also displayed. Digestion was conducted at 37° C. for 15 h.

FIG. 15 provides lipid ion images acquired simultaneously using pre-coated slides of rat brain tissue section. Tentative identifications were based on mass accuracy.

DETAILED DESCRIPTION

Figure 1:
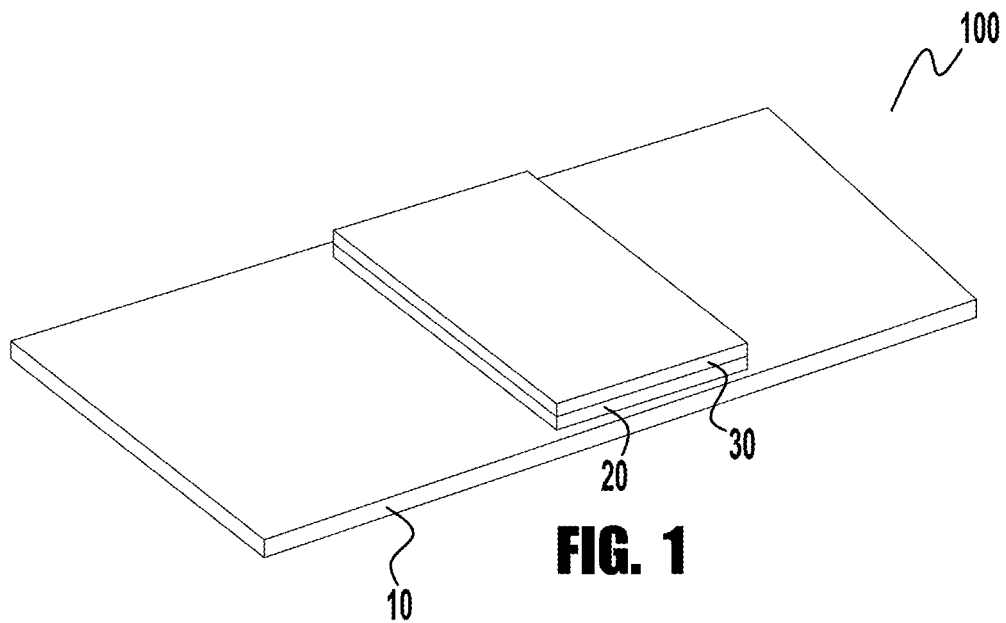
FIG. 1 provides an illustration of a pre-coated analysis substrate bearing an animal tissue specimen.

The present invention provides pre-coated analysis substrates, and methods of making the substrates and using them to analyze animal tissue. The pre-coated analysis substrates can be made by forming a matrix surface on an analysis substrate; adding a protease to the matrix surface to form a pre-coated analysis substrate; and placing an animal tissue specimen on the matrix surface. The animal tissue can then be analyzed by allowing the protease to partially digest the animal tissue specimen; and analyzing the partially digested animal tissue specimen by mass spectrometry.

Definitions

Unless otherwise defined, all technical and scientific terms used herein have the same meaning as commonly understood by one of ordinary skill in the art to which this invention pertains. In case of conflict, the present specification, including definitions, will control.

The terminology as set forth herein is for description of the embodiments only and should not be construed as limiting the application as a whole. Unless otherwise specified, "a," "an," "the," and "at least one" are used interchangeably. Furthermore, as used in the description of the application and the appended claims, the singular forms "a", "an", and "the" are inclusive of their plural forms, unless contraindicated by the context surrounding such. Furthermore, the recitation of numerical ranges by endpoints includes all of the numbers subsumed within that range (e.g., 1 to 5 includes 1, 1.5, 2, 2.75, 3, 3.80, 4, 5, etc.).

Throughout this application, the term "about" is used to indicate that a value includes the standard deviation of error for the device or method being employed to determine the value, except that the value will never deviate by more than 5% from the value cited.

The term "biomolecule(s)" as used herein refers to a protein, a peptide, a nucleic acid, a sugar, or a lipid that exists extracellularly or intracellularly. The term "biomolecule(s)" as used herein may be derived from any living body or organism, such as viruses, prokaryotes, eukaryotes, fungi, plants, higher plants, animals, insects, higher animals, mammals, and humans, or cultured cells or cultured tissues thereof. The term "nucleic acid" included in the biomolecule(s) as used herein refers to a single-stranded or double-stranded nucleic acid(s) containing at least 10, preferably 50, 300, 500, or 1000 or more nucleotides, and preferably interacts with a specific low-molecular-weight compound. A nucleic acid may be DNA or RNA. Examples of RNA include tRNA and ribosome RNA, and ribozyme. Examples of a sugar included in the biomolecule(s) as used herein include polysaccharides that preferably interact with specific low-molecular-weight compounds. Examples of such sugar include proteoglycans or derivatives thereof such as hyaluronic acid, chitin, heparan sulfate, keratan sulfate, dermatan sulfate, sialic acid, and chondroitin sulfate.

As used herein, the term "polypeptide" refers to an oligopeptide, peptide, or protein, or to a fragment, portion, or subunit of any of these, and to naturally occurring or synthetic molecules. The term "polypeptide" also includes amino acids joined to each other by peptide bonds or modified peptide bonds, i.e., peptide isosteres, and may contain any type of modified amino acids. The term "polypeptide" also includes peptides and polypeptide fragments, motifs and the like, glycosylated polypeptides, all "mimetic" and "peptidomimetic" polypeptide forms, and retro-inversion peptides (also referred to as all-D-retro or retro-enantio peptides). Generally, a peptide has less than 30 amino acids, whereas a protein has more than 30 amino acids, though this is an approximate dividing line between the two.

As used herein, the term "lipid" refers to naturally occurring fats, waxes, sterols, monoglycerides, diglycerides, triglycerides, and phospholipids. Examples of the term "lipid" included in the biomolecule(s) as used herein include lipids that are contained in the above illustrated organisms, and preferably interact with specific low-molecular-weight compounds. Examples of such lipid include phospholipids such as a sphingophospholipid and a glycerophospholipid, glycolipids such as a sphingoglycolipid and a glyceroglycolipid, and conjugated lipids that form extracellular or cell membranes, such as a lipoprotein lipid, a sulpholipid and a galactolipid.

The present invention provides pre-coated analysis substrates, and methods of making the substrates and using them to analyze animal tissue. An example of a pre-coated analysis substrate bearing an animal tissue specimen is shown in FIG. 1. The pre-coated analysis substrate 100 includes an analysis substrate 10, such as a glass slide, upon which is formed a matrix surface 20. The matrix surface 20 can include a protease, or in some embodiments, the protease is applied directly to the analysis substrate without a matrix. An animal tissue specimen 30 is placed on top of the matrix surface so that it contacts the protease, causing digestion of the animal tissue which can then be analyzed by mass spectrometry.

Figure 2:
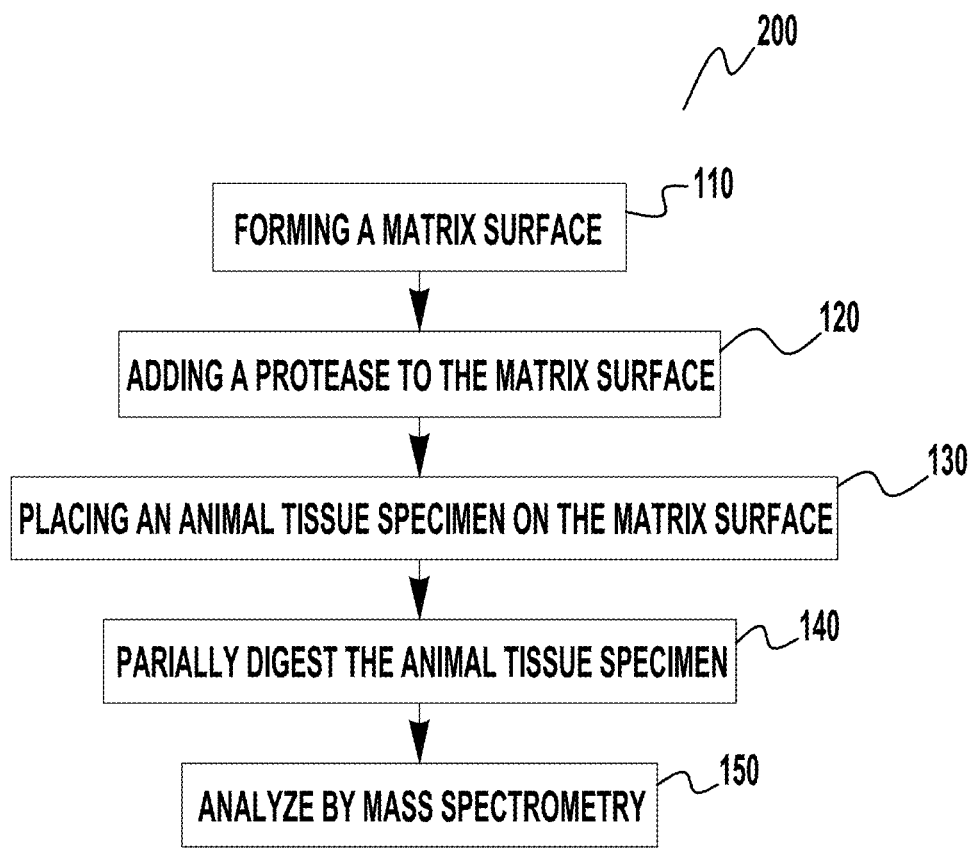
FIG. 2 provides a schematic representation of a method for analyzing animal tissue.

In one aspect, the present invention provides a method for analyzing animal tissue, which is illustrated by FIG. 2. The method 200 includes the steps of forming a matrix surface on an analysis substrate 110; adding a protease to the matrix surface to form a pre-coated analysis substrate 120; placing an animal tissue specimen on the matrix surface 130; allowing the protease to partially digest the animal tissue specimen 140; and analyzing the partially digested animal tissue specimen by mass spectrometry 150.

The steps of forming a matrix surface on an analysis substrate and adding a protease to the matrix surface to form a pre-coated analysis substrate can be carried out in any order. In some embodiments, the protease is first deposited on the analysis substrate and then matrix is added to the deposited protease. In other embodiments, the matrix is first deposited on the surface of the analysis substrate, and then the protease is added to the matrix. In a further embodiment, the protease and the matrix are deposited on the analysis substrate together and simultaneously.

In another aspect, the invention provides a method for analyzing animal tissue using a pre-coated analysis substrate. In this aspect of the invention, a pre-coated analysis substrate is used to carry out the analysis that has already been prepared earlier. Typically, in this aspect, the pre-coated analysis substrate will have been stored for a period of time before use. In this aspect of the invention, the method includes the steps of placing an animal tissue specimen on a matrix surface comprising a protease on an analysis substrate; b) allowing the protease to partially digest the animal tissue specimen; and analyzing the partially digested animal tissue specimen by mass spectrometry.

Analyzing animal tissue refers to determining the level of one or more biomolecules in the animal tissue. The level of the one or more biomolecules may be determined qualitatively or quantitatively. In some embodiments, the digested animal tissue specimen is analyzed for peptide content. In other embodiments, the digested animal tissue specimen is analyzed for lipid content.

The analysis substrate may comprise any suitable surface having a substantially planar surface upon which a matrix may be formed and analysis may be conducted. Exemplary analysis substrates include, but are not limited to, glass slide, a plastic slide, a metal plate, a porous filter material, and a rigid slab. In some embodiments, the analysis substrate is a glass slide, such as a microscope slide. An example of a suitable glass slide is a 1"×3" glass slide, which is a common format for microarray readers; variations in shape and spacing of individual wells were used to encode their specific location within the array. In further embodiments, the glass slide is a conductive indium tin oxide (ITO)-coated slide.

Various aspects of the invention also include the step of forming a matrix surface on an analysis substrate. The matrix chosen will depend on the particular mass spectrometry technique used to analyze the animal tissue. For example, in the case of MALDI-MS, matrix materials are typically solid organic acids. MALDI matrix materials include crystallized molecules such as 3,5-dimethoxy-4-hydroxycinnamic acid (sinapinic acid), α-cyano-4-hydroxycinnamic acid (CHCA) and 2,5-dihydroxybenzoic acid (DHB). Other MALDI matrix materials include 4-hydroxy-3-methoxycinnamic acid (ferulic acid), picolinic acid, and 3-hydroxy picolinic acid. A solution of one of these molecules is made, often in a mixture of highly purified water and an organic solvent such as acetonitrile (ACN) or ethanol. The matrix can be used to tune the mass spectrometer to ionize the sample in different ways. Acid-base-like reactions are often utilized to ionize the sample; however, molecules with conjugated pi systems, such as naphthalene like compounds, can also serve as an electron acceptor and thus a matrix for MALDI/TOF. The matrix density can also have an impact on matrix performance. Accordingly, in some embodiments, the matrix has a density from 0.3 to 3.0 mg/cm$^2$.

The matrix can be formed on the analytic substrate using a variety of methods known to those skilled in the art. For example, the matrix may be applied to the analytic substrate as an aerosolized mixture that is spray-coated onto the slide, either manually or using a robotic sprayer. Preferably, the matrix is applied as a substantially homogenous thin layer, covering an area corresponding roughly in size to the size of the animal tissue specimen.

The matrix used for carrying out MALDI-MS can vary between being an acidic (i.e., crystallized) matrix and an ionic matrix. The ionic matrix is a more liquid, permeable form, whereas the crystallized form provides a better substrate for mass spectrometry. Accordingly, in some embodiments, additional steps are carried out to convert the matrix from one form to another during the analysis method. For example, in some embodiments, after the animal tissue specimen has been placed on the matrix surface, the animal tissue specimen is then hydrated to facilitate interaction between the matrix and the animal tissue specimen. In some embodiments, the animal tissue specimen is hydrated for 5 to 10 minutes. However, after hydration, the matrix is then crystallized before conducting mass spectrometry to provide a better mass spectrometry substrate. Hydration can also include introduction of diisopropylethylamine or a similar compound to convert the matrix into ionic form, while crystallization can include introduction of a strong acid such as trifluoroacetic acid to convert the matrix to an acidic form.

In some embodiments, the matrix is formed as a microarray. In a microarray, portions of matrix mixture can be deposited in a regular pattern in order to facilitate conducting and/or automating the assay. For example, the portions of matrix can be positioned in regularly spaced rows and columns. When conducting the method of tissue analysis, it can be useful to compare the biomolecule (e.g., polypeptide) content from a plurality of spatially discrete regions of the animal tissue. When used as a microarray, the matrix material deposited on the analytic substrate must be of a sufficient size to permit creation of a plurality of microregions, e.g., at least 1 micron to several millimeters, including sizes in between, such as 2 µm, 3 µm, 4 µm, 5 µm, 6 µm, 7 µm, 8 µm, 9 µm, 10 µm, 15 µm, 20 µm, 25 µm, 30 µm, 35 µm, 40 µm, 45 µm, 50 µm, 60 µm, 70 µm, 80 µm, 90 µm, 100 µm, 125 µm, 150 µm, 175 µm, 200 µm, 250 µm, 275 µm, 300 µm, 400 µm, 450 µm, 500 µm, 600 µm, 700 µm, 800 µm, 900 µm, 1000 µm, 2 mm, 3 mm, 4 mm and 5 mm Protease The method also includes adding a protease to the matrix surface to form a pre-coated analysis substrate. As noted herein, the protease can be added to the matrix surface before, after, or simultaneous to matrix deposition. The present invention makes use of a protease (i.e., proteolytic enzyme or proteinase) to facilitate the analysis of an animal tissue specimen. Proteases are involved in digesting long protein chains into shorter fragments by splitting the peptide bonds that link amino acid residues. Examples of proteases include serine proteases, threonine proteases, cysteine proteases, aspartate proteases, glutamic acid proteases, and metalloproteases. Protease digestion serves to release polypeptides from the animal tissue surface, and to digest proteins to facilitate analysis my mass spectrometry.

Most commonly digestions are carried out with the proteases trypsin or lysine specific proteinases, because these enzymes are reliable, specific and produce a suitable number of peptides. The next most common digestion is at aspartate or glutamate using endoproteinase Glu-C or endoproteinase Asp-N. Pepsin or chymotrypsin are also sometimes used. Proteinases of broad specificity may generate many peptides, and the peptides may be very short. The amount of protease used can vary depending on the specifics of the analysis, such as the particular type of protease being used and the type of matrix and mass spectrometry being used. In some embodiments, the protease is present at a concentration from about 1 to 30 $\mu g/cm^2$, while in other embodiments the protease is present at a concentration from about 1 to 10 $\mu g/cm^2$.

In another aspect of the invention, a pre-coated analysis substrate is prepared and then stored for later use. In this aspect, a method of preparing a pre-coated analysis substrate is provided that includes the steps of forming a matrix surface on an analysis substrate; adding a protease to the matrix surface to form a pre-coated analysis substrate; and storing the pre-coated analysis substrate for 24 hours or more before use. A further aspect of the invention is directed to the pre-coated analysis substrate itself, which has been prepared as described herein.

The pre-coated analysis substrate can include any of the characteristics already described for methods of preparing and using a pre-coated analysis substrate. For example, in some embodiments, the matrix comprises α-cyano-4-hydroxycinnamic acid, while in other embodiments the matrix is formed as a microarray. The pre-coated analysis substrate includes an analysis substrate, and a matrix (and/or protease) layer on one face of the analysis substrate.

Storage of Pre-Coated Analysis Substrates

One advantage of the pre-coated analysis substrates of the present invention is their ability to be stored for a significant period of time before use. Preferably, the pre-coated analysis substrates are sealed and chilled during storage. For example, the pre-coated analysis substrates can be stored at a temperature of about 4° C. In some embodiments, the pre-coated analysis substrates are stored for 1 hour or more before use. In other embodiments, the pre-coated analysis substrates are stored for 24 hours or more before use. In further embodiments, the pre-coated analysis substrates are stored for a week or more, a month or more, or 6 months or more before use.

Animal Tissue Specimens

The method analyzing animal tissue also includes the step of placing an animal tissue specimen on the matrix surface. Preferably the animal tissue specimen has a surface area that roughly corresponds in size to the area of the matrix and/or protease placed on the analytic slide. Techniques of mounting tissue onto an analytic substrate are known to those skilled in the art. For example, the tissue can be thaw-mounted on a substrate using a small amount of thermal energy to thaw a portion of frozen tissue.

Intact tissue samples are obtained by standard methodologies for use as animal tissue specimens. In some embodiments, the tissue specimen has a thickness ranging from about 1 μm to about 50 μm, while in other embodiments the tissue specimen has a thickness ranging from about 3 μm to about 10 μm. In some embodiments, the animal tissue specimen is cryosectioned (i.e., frozen) animal tissue, which can be prepared using a cryostat. In other embodiments, the animal tissue specimen has been treated with chemical fixatives to preserve the tissue. Examples of chemical fixatives include formalin (e.g., 4% formaldehyde in phosphate buffered saline) and glutaraldehyde. These fixatives preserve tissues or cells mainly by irreversibly cross-linking proteins. Examples of other fixatives are osmium tetroxide or uranyl acetate. Tissue samples can also include paraffin wax, which is used after water has been removed from tissues to provide a medium that solidifies to allow thin sections of tissue to easily be cut. Accordingly, in some embodiments, the animal tissue specimen is formalin-fixed paraffin-embedded tissue.

Any type of animal tissue can be analyzed. The animal tissue evaluated can be healthy tissue, or it can be tissue that is diseased or injured. Examples of animal tissue suitable for evaluation using the present invention include heart tissue, liver tissue, kidney tissue, prostate tissue, breast tissue, ovary tissue, uterine tissue, skin tissue, lung tissue, brain tissue, colon tissue, pancreatic tissue, and muscle tissue.

Biopsy procedures for obtaining the specimen will generally involve the sterility required of surgical operations, even though the tissues being sample are from cadavers or animals that will be sacrificed. For internal tissues, incisions will be made proximal to the tissue of interest, followed by retraction, excision of tissue and surgical closing of the incision. Superficial tissue sites are accessed by simple excision of the available tissue.

Tissue specimens should be handled such that (a) the integrity of the tissue is maintained and (b) that the cells within the tissue, particularly those in the region(s) where hydrogel portions will be placed are not damaged. Appropriate physiologic buffers are generally applied to the tissue, or the tissues are immersed therein. The tissue may also be cooled to appropriate temperatures for limited periods of time. Steps should be taken to ensure that apoptosis or other cellular degradation will not be induced in the tissue specimen. In some embodiments, pretreatment of the animal tissue specimen prior to analysis may prove advantageous. One useful pretreatment is an ethanol wash, optionally followed by a storage period of minutes to hours.

In another aspect of the invention, animal tissue specimens are analyzed using an analysis substrate that is pre-coated with a protease. In this case, the invention provides a method for analyzing animal tissue that includes the steps of coating a protease on a surface of an analysis substrate to form a pre-coated analysis substrate; placing an animal tissue specimen on the protease coated surface; allowing the protease to partially digest the animal tissue specimen; and analyzing the partially digested animal tissue specimen by mass spectrometry. This method can be useful for methods of surface analysis that do not require the presence of a matrix. However, in other embodiments, the partially digested animal tissue can be coated with matrix before analysis.

This method can be used to evaluate a variety of different biomolecules. In some embodiments, the partially digested animal tissue specimen is analyzed for peptide content, while in other embodiments the partially digested animal tissue specimen is analyzed for lipid content.

Mass Spectrometry

A "mass spectrometer" is an analytical instrument that can be used to determine the molecular weights of various substances, such as proteins and nucleic acids. It can also be used in some applications, e.g., to determine the sequence of protein molecules and the chemical composition of virtually any material. Typically, a mass spectrometer comprises four parts: a sample inlet, an ionization source, a mass analyzer, and a detector. A sample is optionally introduced via various types of inlets, e.g., solid probe, GC, or LC, in gas, liquid, or solid phase. The sample is then typically ionized in the ionization source to form one or more ions. The resulting ions are introduced into and manipulated by the mass analyzer. Surviving ions are detected based on mass to charge ratio. In one embodiment, the mass spectrometer bombards the substance under investigation with an electron beam and quantitatively records the result as a spectrum of positive and negative ion fragments. Separation of the ion fragments is on the basis of mass to charge ratio of the ions. If all the ions are singly charged, this separation is essentially based on mass. Traditional quantitative MS has used electrospray ionization (ESI) followed by tandem MS (MS/MS) while newer quantitative methods are being developed using matrix assisted laser desorption/ionization (MALDI) followed by time of flight (TOF) MS.

A. ESI

ESI is a convenient ionization technique developed by Fenn and colleagues (Fenn et al., Science, 246(4926):64-71, 1989) that is used to produce gaseous ions from highly polar, mostly nonvolatile biomolecules, including lipids. The sample is injected as a liquid at low flow rates (1-10 µL/min) through a capillary tube to which a strong electric field is applied. The field generates additional charges to the liquid at the end of the capillary and produces a fine spray of highly charged droplets that are electrostatically attracted to the mass spectrometer inlet. The evaporation of the solvent from the surface of a droplet as it travels through the desolvation chamber increases its charge density substantially. When this increase exceeds the Rayleigh stability limit, ions are ejected and ready for MS analysis.

A typical conventional ESI source consists of a metal capillary of typically 0.1-0.3 mm in diameter, with a tip held approximately 0.5 to 5 cm (but more usually 1 to 3 cm) away from an electrically grounded circular interface having at its center the sampling orifice. Kabarle et al., Anal. Chem. 65(20):972A-986A (1993). A potential difference of between 1 to 5 kV (but more typically 2 to 3 kV) is applied to the capillary by power supply to generate a high electrostatic field ($10^6$ to $10^7$ V/m) at the capillary tip. A sample liquid carrying the analyte to be analyzed by the mass spectrometer, is delivered to tip through an internal passage from a suitable source (such as from a chromatograph or directly from a sample solution via a liquid flow controller). By applying pressure to the sample in the capillary, the liquid leaves the capillary tip as small highly electrically charged droplets and further undergoes desolvation and breakdown to form single or multicharged gas phase ions in the form of an ion beam. The ions are then collected by the grounded (or negatively charged) interface plate and led through an orifice into an analyzer of the mass spectrometer. During this operation, the voltage applied to the capillary is held constant. Aspects of construction of ESI sources are described, for example, in U.S. Pat. Nos. 5,838,002; 5,788,166; 5,757,994; RE 35,413; 6,756,586, 5,572,023 and 5,986,258.

B. ESI/MS/MS

In ESI tandem mass spectroscopy (ESI/MS/MS), one is able to simultaneously analyze both precursor ions and product ions, thereby monitoring a single precursor product reaction and producing (through selective reaction monitoring (SRM)) a signal only when the desired precursor ion is present. When the internal standard is a stable isotope-labeled version of the analyte, this is known as quantification by the stable isotope dilution method. This approach has been used to accurately measure pharmaceuticals (Zweigenbaum et al., Anal. Chem., 74:2446, 2000) and bioactive peptides (Desiderio et al., Biopolymers, 40:257, 1996). Newer methods are performed on widely available MALDI-TOF instruments, which can resolve a wider mass range and have been used to quantify metabolites, peptides, and proteins. Larger molecules such as peptides can be quantified using unlabeled homologous peptides as long as their chemistry is similar to the analyte peptide. Bucknall et al., J. Am. Soc. Mass Spectrometry, 13(9):1015-27 (2002). Protein quantification has been achieved by quantifying tryptic peptides. Mirgorodskaya et al., Rapid Commun. Mass Spectrom., 14:1226, 2000. Complex mixtures such as crude extracts can be analyzed, but in some instances sample clean up is required. Gobom et al., Anal. Chem. 72:3320, 2000. Desorption electrospray is a new associated technique for sample surface analysis.

C. LESA

Liquid extraction surface analysis mass spectrometry (LESA-MS) is a surface profiling technique that combines micro-liquid extraction from a solid surface with nano-electrospray mass spectrometry. See Eikel et al., Rapid Commun Mass Spectrom. 25(23):3587-96 (2011), which evaluates LESA-MS by examining the distribution and biotransformation of unlabeled terfenadine in mice and comparing the findings to QWBA, whole tissue LC/MS/MS and MALDI-MSI. The spatial resolution of LESA-MS can be optimized to about 1 mm on tissues such as brain, liver and kidney, also enabling drug profiling within a single organ.

D. DESI

DESI is a combination of electrospray (ESI) and desorption (DI) ionization methods. Ionization takes place by directing an electrically charged mist to the sample surface that is a few millimeters away. The electrospray mist is pneumatically directed at the sample where subsequent splashed droplets carry desorbed, ionized analytes. After ionization, the ions travel through air into the atmospheric pressure interface which is connected to the mass spectrometer. DESI-MS offers a number of advantages over traditional MS approaches, including (1) minimal sample preparation; (2) sample maintenance under ambient conditions outside the vacuum system; (3) rapid, high-throughput analysis; (4) the ability for in situ detection; and (5) label-free chemical imaging with basic instrumentation requirements. See Ifa et al., Analyst. 135:669-681 (2010).

E. MALDI-TOF-MS

In some embodiments, the mass spectrometry is matrix-assisted laser desorption/ionization (MALDI) mass spectrometry. Since its inception and commercial availability, the versatility of MALDI-TOF-MS has been demonstrated convincingly by its extensive use for qualitative analysis. For example, MALDI-TOF-MS has been employed for the characterization of synthetic polymers, peptide and protein analysis (Zaluzec et al., Protein Expr. Purif., 6:109, 1995; Roepstorff et al., EXS, 88:81, 2000), DNA and oligonucleotide sequencing, and the characterization of recombinant proteins. Recently, applications of MALDI-TOF-MS have been extended to include the direct analysis of biological tissues and single cell organisms with the aim of characterizing endogenous peptide and protein constituents. Li et al., Trends Biotechnol., 18:151 (2000); Caprioli et al., Anal. Chem., 69:4751 (1997).

The properties that make MALDI-TOF-MS a popular qualitative tool—its ability to analyze molecules across an extensive mass range, high sensitivity, minimal sample preparation and rapid analysis times—also make it a potentially useful quantitative tool. MALDI-TOF-MS also enables non-volatile and thermally labile molecules to be analyzed with relative ease. It is therefore prudent to explore the potential of MALDI-TOF-MS for quantitative analysis in clinical settings, for toxicological screenings, as well as for environmental analysis. In addition, the application of MALDI-TOF-MS to the quantification of polypeptides (i.e., peptides and proteins) is particularly relevant. The ability to quantify intact proteins in biological tissue and fluids presents a particular challenge in the expanding area of proteomics and investigators urgently require methods to accurately measure the absolute quantity of proteins. While there have been reports of quantitative MALDI-TOF-MS applications, there are many problems inherent to the MALDI ionization process that have restricted its widespread use. Wang et al., J. Agric. Food. Chem., 48:3330 (2000); Desiderio et al., Biopolymers, 40:257 (1996). These limitations primarily stem from factors such as the sample/matrix heterogeneity, which are believed to contribute to the large variability in observed signal intensities for analytes, the limited dynamic range due to detector saturation, and difficulties associated with coupling MALDI-TOF-MS to on-line separation techniques such as liquid chromatography. Combined, these factors are thought to compromise the accuracy, precision, and utility with which quantitative determinations can be made.

Because of these difficulties, practical examples of quantitative applications of MALDI-TOF-MS have been limited. Most of the studies to date have focused on the quantification of low mass analytes, in particular, alkaloids or active ingredients in agricultural or food products, whereas other studies have demonstrated the potential of MALDI-TOF-MS for the quantification of biologically relevant analytes such as neuropeptides, proteins, antibiotics, or various metabolites in biological tissue or fluid. Muddiman et al., Fres. J. Anal. Chem., 354:103 (1996); Nelson et al., Anal. Chem., 66:1408 (1994). In earlier work it was shown that linear calibration curves could be generated by MALDI-TOF-MS provided that an appropriate internal standard was employed. Duncan et al., Rapid Commun. Mass Spectrom., 7:1090 (1993). This standard can "correct" for both sample-to-sample and shot-to-shot variability. Stable isotope labeled internal standards (isotopomers) give the best result.

With the marked improvement in resolution available on modern commercial instruments, primarily because of delayed extraction (Bahr et al., J. Mass. Spectrom., 32:1111, 1997), the opportunity to extend quantitative work to other examples is now possible; not only of low mass analytes, but also biopolymers. Of particular interest is the prospect of absolute multi-component quantification in biological samples (e.g., proteomics applications).

Extraction and Sample Preparation

In some embodiments, an extraction step is carried out to extract the biomolecules from the digested mixture in order to provide an extract for analysis by mass spectrometry. For example, in some embodiments, peptides are extracted from the animal tissue specimen using solvent extraction prior to analyzing the partially digested animal tissue specimen by mass spectrometry. The extraction step can include an organic extraction and/or an aqueous extraction. Extraction will shrink and swell the matrix and tissue sample in order to release biomolecules (e.g., peptides) within the digested mixture, and can also separate the polypeptides, which migrate to the aqueous phase, from other components in the extraction mixture.

In the case of peptide analysis, proteins should be extracted from lipids, metabolites, and other non-proteinaceous compounds, which may interfere with downstream procedures. Various chemical precipitation methods are available for protein isolation; these include acetone, trichloroacetic acid (TCA), ethanol, isopropanol, chloroform/methanol, and ammonium sulfate. The efficiency of protein precipitation varies among different organic solvents. For example, acetone has been determined to precipitate more acidic and hydrophilic proteins, whereas ultracentrifugation fractionates more basic, hydrophobic, and membrane proteins. Thongboonkerd et al., Kidney Int. 62(4):1461-9 (2002). Alternatively, chloroform methanol extraction has been used to successfully extract hydrophobic proteins. Stark et al., Eur J Biochem. 266(1):209-14 (1999). Precipitation strategies can be optimized for a particular sample type. In some embodiments, it may be preferable to treat the polypeptide extract with various enzymes (lipases, collagenases, proteases, nucleases) to further purify the sample.

Automation and High-Throughput Analysis

In some embodiments of the invention, one or more steps of the method can be automated and implemented for the analysis of a very large number of samples. For example, the step of applying the protease and/or the matrix to the analytic substrate can be done robotically. Likewise, removing the digested mixture and extracting the polypeptides can be done robotically. Commercially available mass spectrometry system (e.g., MALDI instruments) can record the mass spectra of all the extract samples in quick succession. The analysis of the data can also be automated by employing a computer program to analyze generated data. With sufficient automation, a single person, with access to a MALDI instrument could use the automated techniques to measure as many as 1000 samples per day.

In some embodiments, the one or more portions of the animal tissue specimen are placed in a regular column and row pattern (e.g., corresponding to that found in a standard 96 well plate) in a highly automated fashion, thereby ensuring that the rate of screening is dependent only on the speed of sequential analysis of the mass spectrometer. An automatic sampler can be used to transport samples between the purification system (which includes extraction and/or column purification) and the mass spectrometer. Autosamplers can be purchased from standard laboratory equipment suppliers such as Gilson and CTC Analytics. Such samplers function at rates of about 10 seconds/sample to about 1 min/sample. In some embodiments, the invention also includes a computer and software operably coupled to the apparatus for recording and analyzing mass spectrometer data and for controlling the automatic sampler.

In some embodiments, the method of analysis using a pre-coated analysis substrate is a high-throughput method. "High throughput mass spectrometry" is used herein to refer to a mass spectrometry system that is capable of analyzing samples at a rate of from about 100 or 200 samples per day to about 15,000 samples per day. In general, mass spectrometry and MALDI-MS in particular have proven to be highly amenable to high throughput applications in both clinical and basic research settings. For example, Sequenom Inc. (San Diego, Calif.) has established MALDI-MS as an effective technique in the field of genotype profiling, and is providing diagnostic products in this area. In some embodiments, the method is capable of analyzing about 200 samples in less than an hour, e.g., 200 samples are injected into a mass spectrometer and analyzed in less than an hour. High throughput screening preferably takes advantage of the ability to automate the data acquisition and data analysis methods.

Imaging the Animal Tissue Specimen

In some embodiments, the method of analyzing animal tissue also includes imaging the partially digested animal tissue specimen that has been analyzed. Once the levels of the one or more biomolecules have been determined, they can be displayed in a variety of ways. For example, the biomolecule levels can be displayed graphically on a display as numeric values or proportional bars (i.e., a bar graph) or any other display method known to those skilled in the art. The graphic display can provide a visual representation of the amounts of the one or more biomolecules in the tissue specimens being evaluated. In addition, in some embodiments, the imaging device can also be configured to display a comparison of the levels of the one or more biomolecules to corresponding control values.

Imaging can also include more sophisticated representations of biomolecule levels. In the context of Mass Spectrometry, imaging refers to techniques used to visualize the spatial distribution of biomolecules by their molecular masses using a two-dimensional map of the animal tissue specimen. The image is generated by taking the data obtained through mass spectrometric analysis of the animal tissue specimen, running it through software, and displaying the resulting image using an optical display device such as a flat panel liquid-crystal, plasma, or light-emitting diode display.

Applications

Alterations in biomolecules (e.g., protein) abundance, structure, or function, act as useful indicators of pathological abnormalities prior to development of clinical symptoms and as such are often useful diagnostic and prognostic biomarkers. The analysis of polypeptide content of animal tissue can be used for various different purposes. Hanash, S., Nature 422, 226-232 (2003). For example, by examining the proteome of various tissues, one can identify subjects that have or are at risk of disease, including infections, cancer, autoimmune disorders, diabetes, or virtually any other condition for which protein aberrations are known. In many cases, the underlying mechanisms of diseases such as cancer are quite complicated in that multiple dysregulated proteins are involved. In other embodiments, analysis of biomolecule content of animal tissue can be used in drug development to identify regulated targets and evaluate drug effects.

In another aspect, the present invention analyzes the biomolecules content of animal tissue using mass spectrometry in order to diagnosis or predict conditions or disease states in a subject. Ideally, the use of the present invention permits replicate sampling to ensure accuracy, but also permits testing for multiple targets in discrete but spatially related portions of a tissue. Tissue samples may be obtained using protocols described herein.

Conditions that may be diagnosed according to the present invention include, but are not limited to, cancer, infection, congenital disease, exposure to toxicity, and diabetes. Generally, the protein expression of one or more protein targets in the tissue sample will be compared in a standard or known expression level, array or distribution. Alternatively, known healthy tissue may be interrogated in parallel to provide the "normal control" to which the sample is compared.

In another embodiment, the present invention permits the monitoring of disease development, disease progression, or the effects of a treatment on a subject. Such an assay will comprise, essentially, the same steps a diagnostic method with the exception that the timing of the examination will be based on (a) a previous negative diagnostic result, (b) a previous positive diagnostic result, or (c) a prior treatment application.

A subject can be any animal, and animal tissue described herein can be obtained from any type of subject. In some embodiments, the subject is a mammal, such as a domesticated farm animal (e.g., cow, horse, pig) or pet (e.g., dog, cat). More preferably, the subject is a human. When the subject is a human, the subject may also be referred to as a patient, particularly when the subject is being evaluated in a medical environment or by medical personnel.

The present invention is illustrated by the following examples. It is to be understood that the particular examples, materials, amounts, and procedures are to be interpreted broadly in accordance with the scope and spirit of the invention as set forth herein.

EXAMPLES

Example 1

Pre-Coated Surfaces for Protein Digestion and Peptide Imaging

One of the challenges with the pre-coated slides is that the tissue cannot be solvent-washed to remove unwanted species once it is placed onto the pre-coated slide. As a result, lipids and lipid dimers were dominant in the obtained mass spectra. A couple of approaches are suggested to address this issue. First, whole organs could be immersed in ethanol solution immediately after extraction from the animal to remove lipids prior to freezing the sample. A second approach would involve chemically linking the trypsin to the surface making it resistant to solvent washes. Ma et al. have suggested the fabrication scheme for such a surface. Ma et al., Anal. Chem. 80, 2949-2956 (2008). Tetraethoxysilane and 3-amino-propyltriethoxysilane were reacted together to form a monolith network. Glutaraldehyde was used to couple the monolith support with trypsin. The immobilized trypsin had significantly higher activity relative to trypsin in-solution. These surfaces can be adapted for the pre-coated approach whereby tissue section is mounted onto these immobilized surfaces, and the slide is solvent washed to remove lipids and salts, incubated to digest proteins, and coated with matrix.

The approach described herein involves the sequential coating of an indium tin oxide (ITO) slide with a matrix and trypsin (e.g., using a robotic sprayer) in advance of providing the tissue. Onto the pre-coated slide, a thin (3-4 µm) section of frozen tissue is then thaw-mounted directly. The slide is placed in a chamber saturated with diisopropylethylamine and water to allow the acidic matrix (CHCA) to convert into an ionic liquid. This conversion provides a suitable pH and liquid environment for tryptic digestion. The slide is then rinsed with a strong acid to return the CHCA matrix to its solid form. Peptides fragments generated during the trypsin digestion are then imaged directly from the slide using MALDI-IMS. Here we demonstrate the ability of matrix and trypsin pre-coated targets to digest proteins in rat brain samples and show the co-localization of generated daughter peptides as confirmation of the method.

Experimental Section

Materials: Acetonitrile (ACN), trifluoroacetic acid (TFA), α-cyano-4-hydroxycinnamic acid (CHCA), diisopropylethylamine (DIEA), trypsin from bovine pancreas, and cytochrome c from the equine heart were purchased from Sigma-Aldrich (St. Louis, Mo.). Conductive indium tin oxide (ITO)-coated microscope slides were purchased from Delta Technologies (Loveland, Colo.). Frozen rat brain was obtained from Pel-Freez (Rogers, Ark.) and stored at −80° C.

Digestion of Protein Standard: A test solution of ionic matrix consisting of 50 µM CHCA and 100 µM DIEA was prepared in water. Cytochrome C and trypsin at 10 µM and 0.5 µM, respectively, were added to allow digestion. After incubation for 24 h at 37° C., 1 µL of the solution was spotted onto a MALDI target. Cold 10% TFA in water (0° C.) was spotted onto sample to convert the ionic matrix into its crystalline form. After 1 min of contact, the acid solution was decanted, and the MALDI plate was dried in a desiccator prior to analysis using a Bruker Ultraflextreme MALDI-TOF in reflectron mode.

Slide Fabrication: Matrix and trypsin are sequentially spray-coated on an ITO-coated glass slide using a HTX™ Sprayer (HTX Technologies, LLC, Chapel Hill, N.C.). CHCA was dissolved in a 9:1 acetonitrile:water solution at 10 mg/mL. To deposit the matrix, the sprayer was operated at a 0.2 mL/min flow rate using a HPLC pump, a 2 mm track spacing, a 1000 mm/min nozzle velocity, a 70° C. nozzle temperature, a 6 psig nebulizer pressure, and 90% ACN as a pushing solvent. The number of passes was varied between 10 to 20 to control the thickness of the matrix coating.

In a second step, trypsin as a 2 mg/mL solution in water was sprayed on top of the matrix coating. A syringe pump was used to accommodate the flow rate of 30 µL/min used for trypsin deposition. The sprayer conditions were 2 mm track spacing, 1000 mm/min nozzle velocity, 30° C. nozzle temperature, 6 psig nebulizer pressure, and water as a pushing solvent. The number of passes was varied between 4 to 12 to control the density of trypsin.

Tissue Mounting: Frozen rat brain tissue was sectioned to 4 µm at −20° C. using a Leica CM 3050S cryostat (Leica Microsystems GmbH, Wetzlar, Germany). A pre-coated slide in the cryostat chamber was warmed for 2 s using a finger and placed directly on top of the sectioned tissue. The tissue adhered to the slightly warmer slide in preference to the cold metal plate. The tissue was then thaw-mounted on the slide using thermal energy from the finger.

In situ Tryptic digestion: The mounted tissue section was placed in a chamber saturated with diisopropylethylamine for 5 min to convert CHCA into its ionic liquid form. After conversion, the slide was placed in a plastic petri dish, sealed with tape, and kept in an oven for 3-16 h at 37° C. After cooling to room temperature, the slide was immersed in a solution of 10% TFA at 0° C. for 1 min to return the matrix to its crystalline form. The slide was dried in a desiccator before MALDI analysis.

MALDI IMS: Imaging experiments were performed using a 15T Bruker MALDI FTICR mass spectrometer (Bruker Daltonics, Billerica, Mass., USA). The instrument is equipped with an Apollo II dual MALDI/ESI ion source and a Smartbeam II 2 kHz Nd:YAG (355 nm) laser. All images were collected using the small laser setting (~50 µm) with a pixel spacing of 100 µm in both x and y directions. Data were collected from m/z of 500 to 4000 with a resolving power of 130,000 at 1000 m/z. External calibration was performed prior to analysis using CsI clusters. FlexImaging 5.0 (Bruker Daltonics) was used to visualize ion images.

In-gel tissue extraction and LC-MS analysis: Polyacrylamide hydrogels were fabricated using previously described procedures. Harris, G. A. et al., Anal. Chem. 85, 2717-2723 (2013); Taverna, D. et al., Anal. Chem. 87, 670-676 (2015). A cylindrical piece of polyacrylamide gel measuring 2 mm in diameter and 2 mm in height was loaded with trypsin and placed onto the cerebellum region of a brain tissue section for 4 h. The gel was removed from the tissue and placed in an Eppendorf tube into which an extracting solution containing 50% ACN and 5% formic acid was pipetted to fully cover the hydrogel. After 15 min of gentle agitation, the solution was collected and replaced by a 100 mM ammonium bicarbonate solution. The Eppendorf tube was agitated for 15 min to re-swell the gel. This process of extraction and re-swelling was repeated 2 additional times. The extracts were dried down and reconstituted in 0.1% formic acid. The solution was analyzed using LC-MS/MS, and the results were analyzed using Scaffold 4.2.1 (Proteome Software, Portland, Oreg.).

Identification of tryptic peptides: Using the results from LC-MS/MS experiment, 20 most abundant proteins in the tissue sample were found based on unique spectra count. For each of the abundant proteins, tryptic peptide sequences were generated allowing for up to 2 missed cleavages using Mmass Peak picking from FTICR average spectrum was performed in Mmass software, and this peak list was compared to the tryptic peptides list based on accurate mass allowing for up to 5 ppm error. Ion images were generated for selected matched peptides.

Results and Discussion

Fabrication and Application of the Pre-Coated Slides

The advantage of pre-coated slides is that the matrix and enzyme can be applied prior to tissue. The slides can be prepared in batches and many samples prepared in a single experiment. In a typical preparation, matrix and trypsin were sequentially spray-coated onto an ITO-coated glass slide in two steps using a HTX™ Sprayer, as shown schematically in FIG. 3(a). Typical CHCA and trypsin densities were ~0.35 mg/cm$^2$ and 30 µg/cm$^2$, respectively. Peptide signals from tissue samples were significantly lower when the enzyme and matrix were mixed and sprayed in one step compared to the case where enzyme and matrix were sprayed sequentially.

The amount of expected CHCA deposited on a slide was calculated based on instrumental conditions using the equation below:

$$\text{Mass deposited} = \frac{\text{\# of passes} \times conc \times \text{flow rate}}{\text{track spacing} \times \text{stage velocity}} \quad \text{(Equation 1)}$$

In practice, a fraction of the aerosolized matrix was deposited away from the slide. Table 1 compares the ratio of actual coverage of CHCA with that calculated using equation 1. The ratio of actual and calculated density is defined as deposition efficiency. Flow rate was 0.2 mL/min in all cases. The ratio of the actual and calculated coverages is defined as deposition efficiency. The deposition efficiency of the matrix application depended on both the nozzle temperature and the nebulizing pressure. The efficiency of the process increases from 44% to 74% as the pressure is reduced from 13 psig to 6 psig while the temperature is kept constant at 30° C. (cases 1 and 2). Again, the efficiency improves from 35% to 47% as the pressure is reduced from 13 psig to 10 psig while the temperature is kept constant at 70° C. (cases 3 and 4). As the nozzle temperature was increased from 30° C. to 70° C. while the pressure was kept constant at 13 psig, the efficiency of the process was reduced from 44% to 35%. Thus, lower temperature and pressure result in high efficiency.

Lower pressure and temperature resulted in wet spraying conditions which lead to inhomogeneous coating, particularly large crystal size. Due to a tradeoff between high efficiency and the homogeneity of the coating, a moderate pressure and temperature must be used. In particular, a temperature of 70° C. and a pressure of 10 psig produced a homogenous coating with modest efficiency.

TABLE 1

Comparison of actual matrix density with calculated density for spray-coated slides.

| Temp. (° C.) | Pressure (psig) | Deposition Efficiency |
|---|---|---|
| 30 | 13 | 44% |
| 30 | 6 | 74% |
| 70 | 13 | 35% |
| 70 | 10 | 47% |

The use of a pre-coated slide for tissue analysis is shown schematically in FIG. 3(b). A thin tissue section was sectioned and thaw-mounted directly on top of a pre-coated slide. The slide was then placed in a chamber saturated with DIEA and water (5 min) during which the matrix turned into yellowish viscous liquid. After conversion to an ionic liquid, the slide was incubated in a sealed petri dish at 37° C. Tryptic peptides were observed using incubation time as short as 3 hours; however, overnight incubation yielded greater extent of digestion as evidenced by greater signal intensities. After incubation, the slide was immersed in cold (~0° C.) 10% TFA for 1 min to remove DIEA and return CHCA to its crystalline state.

Effect of Matrix Concentration on the Peptide Spectra

Figure 4:
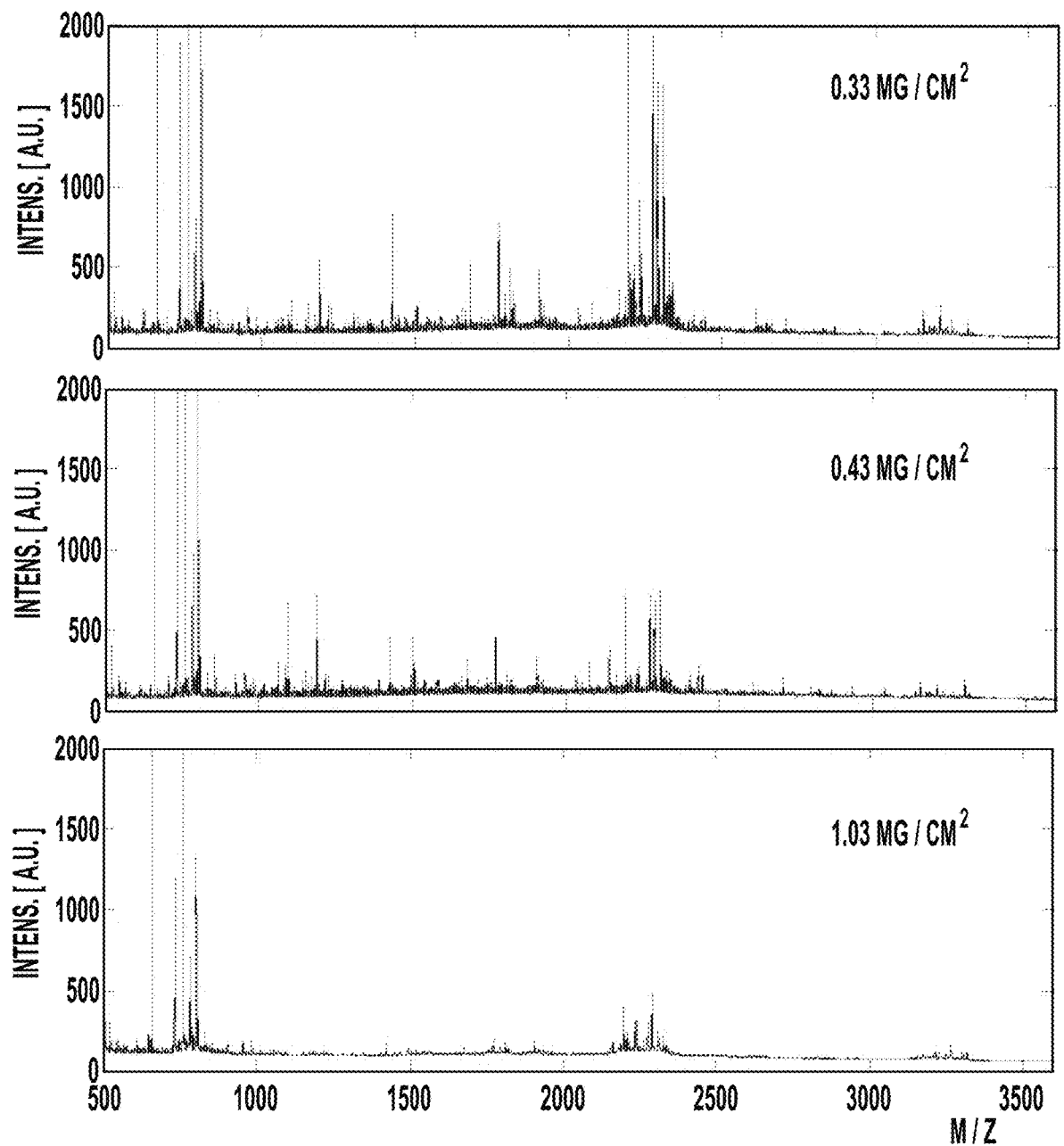
FIG. 4 provides mass spectrometry images demonstrating the effect of matrix concentration on peptide signal from rat brain tissue. Trypsin concentration was 15 µg/cm² in each case, and the tissue thickness was 4 µm. Digestion was done for 3 h at 37° C. Data were collected on Bruker Rapiflex MALDI-TOF.

Yang et al. found that matrix density on a pre-coated substrate affected the signal intensities for both proteins and lipids. Yang, J. H. et al., Anal. Chem. 85, 2907-2912 (2013); Yang, J. H. and Caprioli, R. M., J. Mass Spectrom. 49, 417-422 (2014). For proteins, 1.1 mg/cm$^2$ or higher densities provided a good signal, but slides with lower matrix densities had reduced performance. For lipids, optimal matrix density was 0.3-0.4 mg/cm$^2$. Since peptides have mass ranges between proteins and lipids, we expected the optimal density to be between 0.3-1 mg/cm$^2$. In our experiments, CHCA concentrations in that range were examined as shown in FIG. 4. Trypsin concentration was held constant at 15 μg/cm$^2$ and 4 μm thick rat brain sections were used in all three cases. Strong lipid signals between m/z 600-800 were observed for all three conditions. We were particularly interested in peptide signals between 900-3000 Da. We found that concentration between 0.3-0.4 mg/cm$^2$ provided the best peptide signals. Further reduction in matrix concentration was not feasible as the coverage becomes incomplete after conversion to the crystalline matrix. We hypothesize that the additional matrix reduces the effective trypsin concentration and thus lowers peptide signals. Alternatively, the thicker coatings are not fully converted to ionic matrix after 5 minutes causing non-optimal pH for digestion.

Effect of Trypsin Concentration on Peptide Signal

Figure 5:
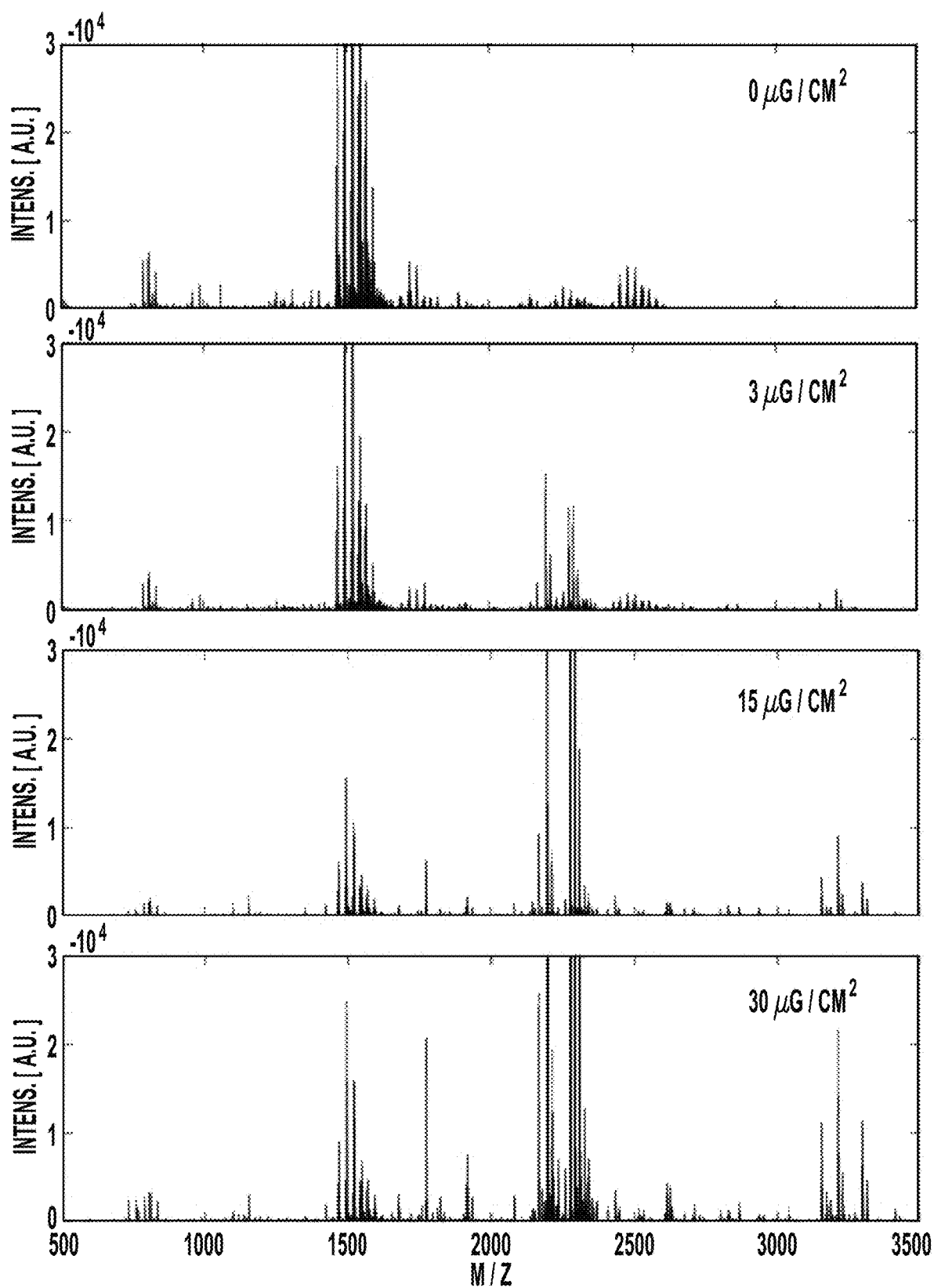
FIG. 5 provides mass spectrometry images exhibiting the effect of trypsin concentration on mass spectra obtained from rat brain tissue sections prepared using the pre-coated slides. Trypsin densities at the surface were: 0 µg/cm², 3 µg/cm², 15 µg/cm², and 30 µg/cm²; CHCA density was 0.37 mg/cm². Digestions were conducted at 37° C. for 4 h.

The amount of trypsin is an important parameter in controlling the rate and extent of digestion. Previous studies employing robotic spotters to deposit matrix and trypsin on tissue samples found that the optimal trypsin concentration was in the range 2-5 μg/cm$^2$. Andersson, M. et al., Nat. Meth. 5, 101-108 (2008). Multiple passes of trypsin spotting were employed to enable optimal extraction. Since repeated extraction is not possible with pre-coated slides, we anticipated that higher concentration of trypsin would be needed. To address this issue, we investigated a range of enzyme concentrations from 0 to 30 μg/cm$^2$, where the matrix density (0.37 mg/cm$^2$) and digestion conditions (4 h at 37° C.) were held constant. Representative average spectra in FIG. 5 show the changes effected by trypsin concentration. Without any enzyme, some signals are seen on m/z values between 700 and 900 Da that correspond to lipids. The strongest signals in the spectrum are from lipid dimers and appear between 1400 and 1700. As the trypsin concentration was increased from 0 to 30 μg/cm$^2$, the relative intensity of the lipid dimers decreased in the spectra. This decrease is due to an increased intensity of other signals from generated peptides. In the spectra, the peptide signals were strongest with an enzyme concentration of 30 μg/cm$^2$, although a trypsin concentration of 15 μg/cm$^2$ also yielded good signal. Increases in trypsin concentration above 30 μg/cm$^2$ are not recommended due to disproportionate increases in signals due to autolysis signals that complicate measurement of peptide signals from tissue.

Optimizing Hydration Time On-Tissue

Figure 6:
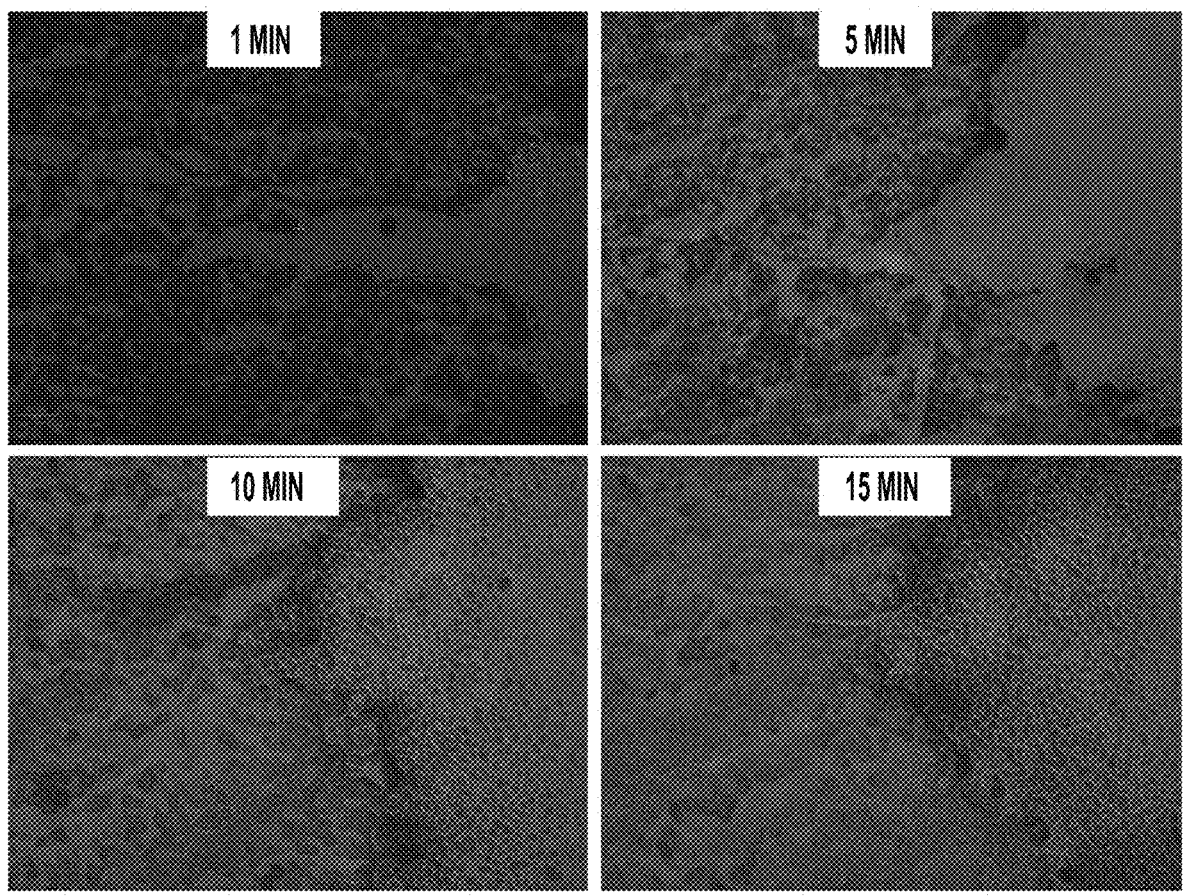
FIG. 6 displays optical images of serial rat brain tissue sections after hydration for different time lengths.

The pre-coated slides are inserted in a glass container that is saturated with DIEA vapor to convert the acidic matrix to ionic matrix. The extent of conversion is directly dependent on the time in the hydration chamber. If the hydration time is too short, then the pH is likely acidic preventing activation of trypsin. If the hydration time is too long, the peptides may delocalize reducing the spatial resolution. Slides were placed in hydration chamber for a time ranging from 1 to 15 min to determine the optimal hydration time. FIG. 6 shows the optical images for each condition after 20 hours of digestion with a 4 μm tissue section. After 1 min of hydration, the top layer of the matrix is converted to ionic liquid while the majority of the matrix remains in the crystalline form. The optical image shows dark tissue on top of the matrix coating. As the time of hydration increases, greater fraction of the crystalline matrix is converted into the ionic liquid promoting greater mixing between the tissue and the liquid. In the presence of ionic liquid, the tissue appears more transparent.

Figure 7:
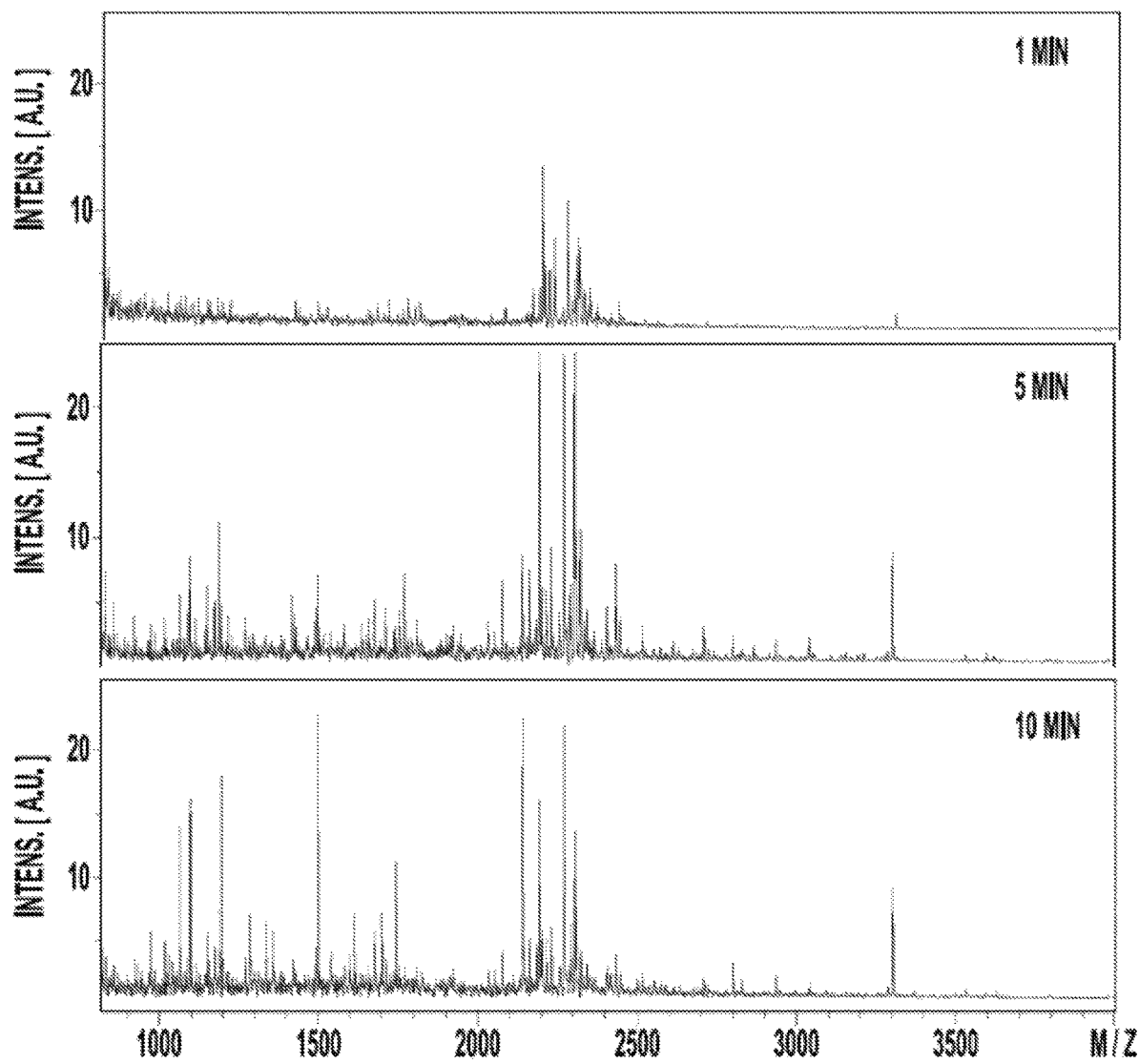
FIG. 7 provides mass spectrometry images acquired from rat brain tissue sections using the pre-coated slides after hydration for different time lengths.

FIG. 7 shows the mass spectrum for each of the conditions acquired using a MALDI-TOF/TOF instrument. After 1 min of hydration, very few peaks are observed. After 5 min, significantly more peaks were observed between m/z 800-4000. After 10 min, the peak intensity increased further for some of the peptides. We compared the relative ion intensity of tryptic peptides from myelin basic protein to make a more detailed comparison. The results are shown in Table 2 for 5 min and 10 min hydration. For the four selected peptides, 10 min hydration yields higher signal-to-noise ratio. In particular, for m/z at 1502.77 and 2141.08, the signal-to-noise ratio was about 3 times greater for the 10 min hydration relative to 5 min hydration. Based on the spectral quality and the tabulated data, we can conclude that 1 min hydration provided minimal digestion, and 10 min hydration yielded greater extent of digestion relative to 5 min hydration.

TABLE 1

Tryptic fragments of myelin basic protein.

| 5 min | | 10 min | |
|---|---|---|---|
| m/z | S/N, | m/z | S/N, 10 min |
| 861.44 | 4.6 | 1019.55 | 5.2 |
| 1502.77 | 8.8 | 1502.77 | 25.8 |
| 2141.08 | 6.1 | 2141.11 | 22.6 |
| 2933.50 | 4.9 | 2933.50 | 4.1 |

Figure 8A:
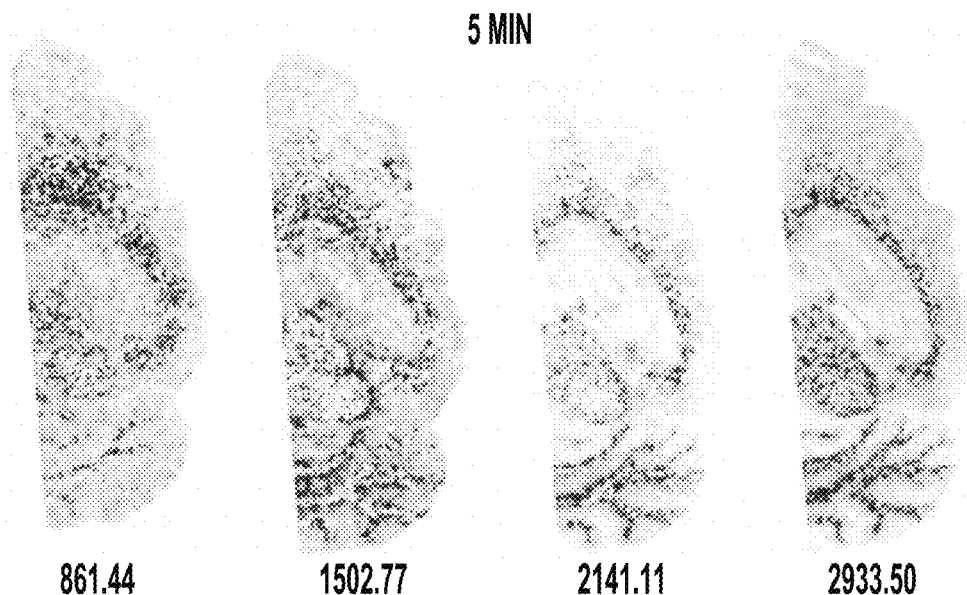
FIGS. 8A and 8B provide images of tryptic peptides of myelin basic protein from serial rat brain tissue sections after 5 min (a) and 10 min (b) of hydration. Hydration was conducted in a chamber saturated with DIEA and water.
Figure 8B:
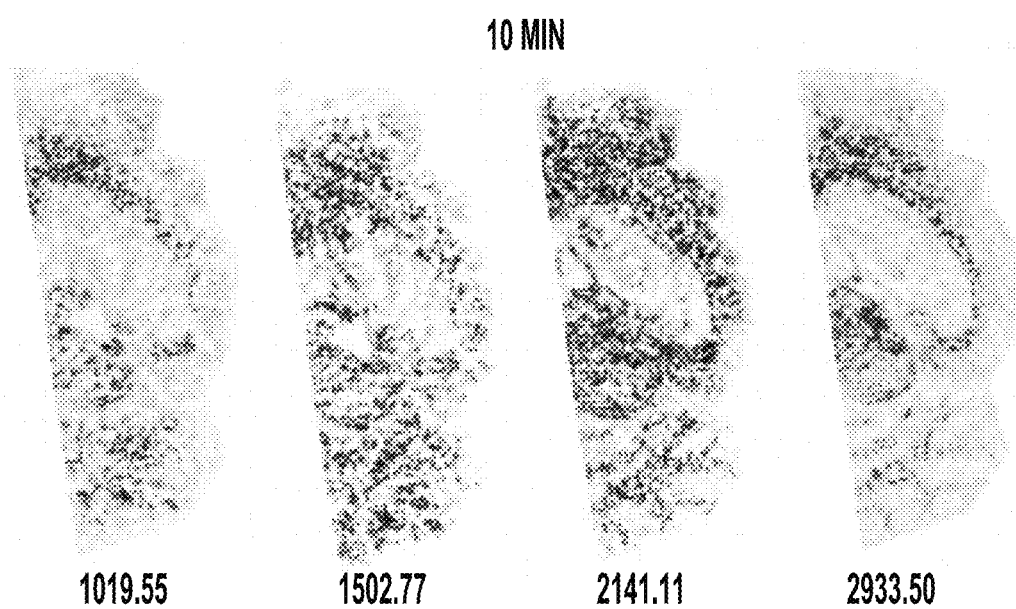

FIG. 8 compares the spatial localization after 5 min and 10 min hydration of the tissue section. The finger-like structures in the cerebellum region of the brain are well defined for 5 min hydration. However, for 10 min hydration, these structures have poor localization. Thus, 5 min hydration provides a good balance between localization and extent of digestion.

Hydration During Incubation

In a conventional post-coated experiment, moist conditions are used within the incubation chamber. A wet paper towel is typically included to provide a source of moisture. For pre-coated slides, experiments with and without water in the incubation chamber were conducted. In one experiment, a dry incubation was used, and the temperature was maintained at 37° C. In the second experiment, same incubation conditions were used except that 2 mL of water was spotted on a wet paper towel. The slide placed in wet incubation chamber looked visibly wet after removal from oven.

Figure 9A:
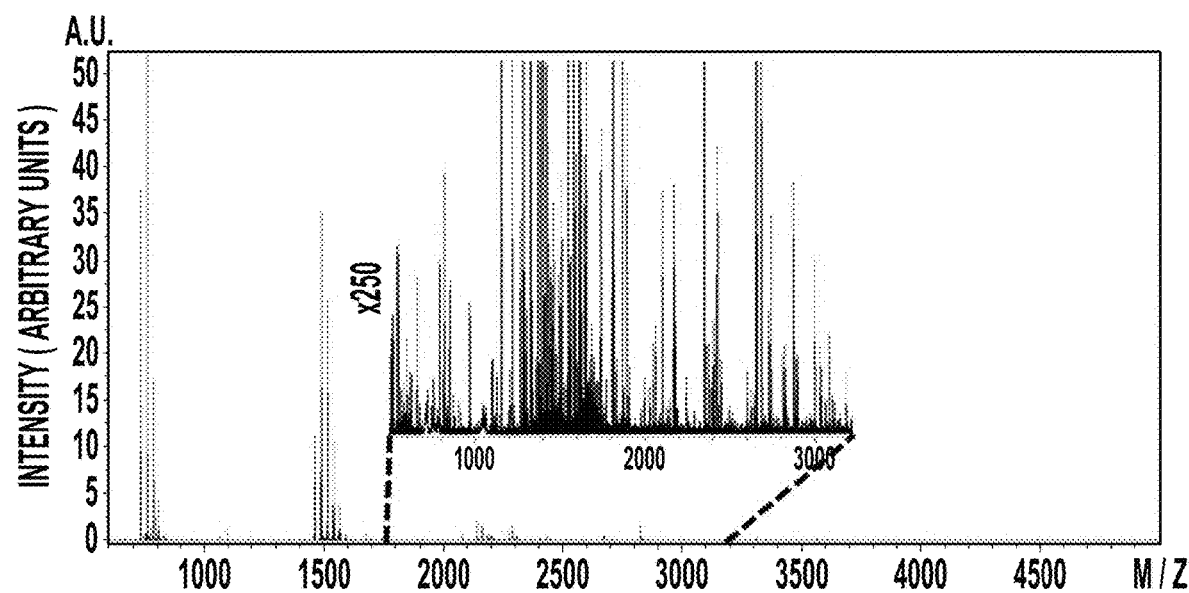
FIGS. 9A and 9B provide mass spectrometry images acquired from serial rat brain tissues sections.
Figure 9B:
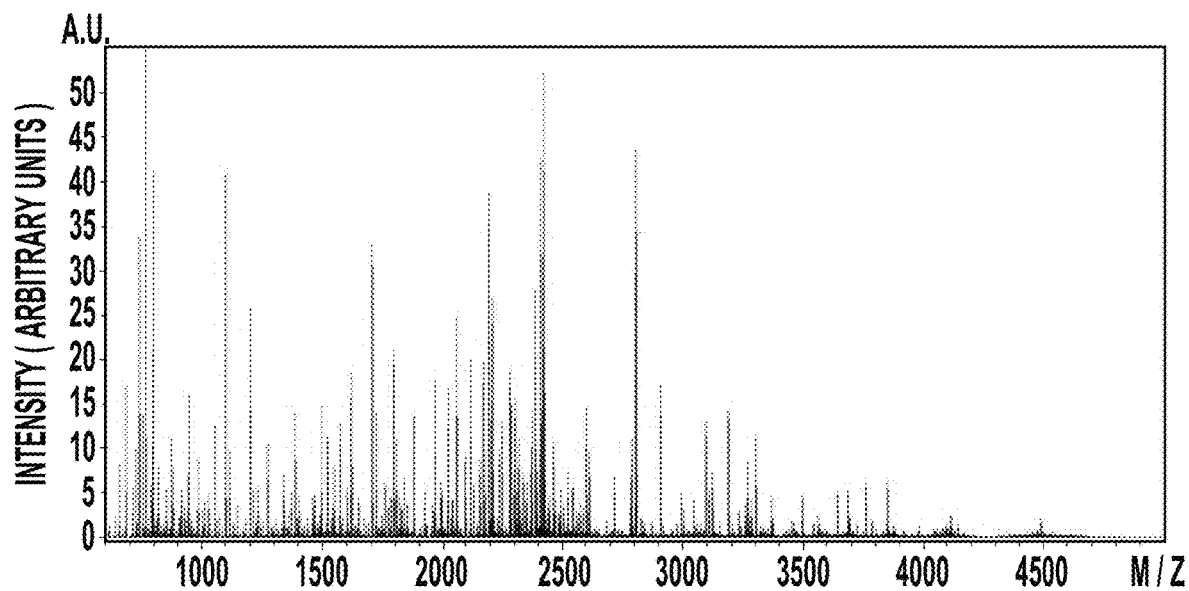

FIG. 9 compares the average mass spectra for both cases. The spectrum corresponding to the dry incubation was dominated by lipid signals. Peptide signal was only observed when the spectrum was enlarged as shown in the inset. The spectrum corresponding to a wet incubation chamber showed significantly more peptides without any zoom indicating that the relative concentration of tryptic peptides was much higher.

Figure 10A:
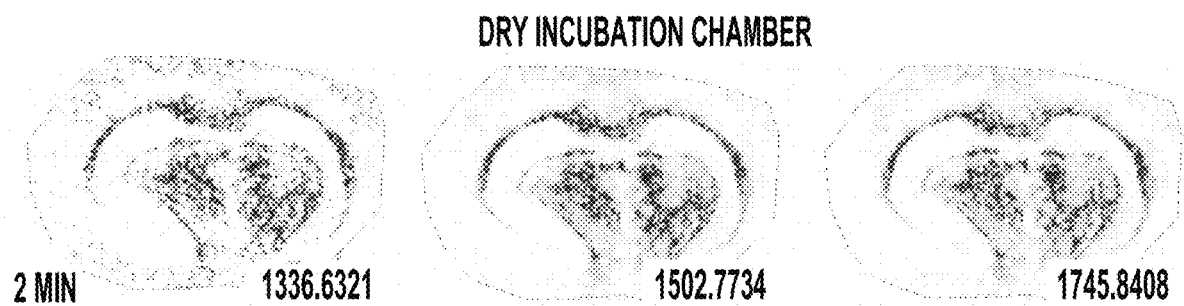
FIGS. 10A and 10B provide ion images of samples performed in dry and wet incubation chambers.
Figure 10B:
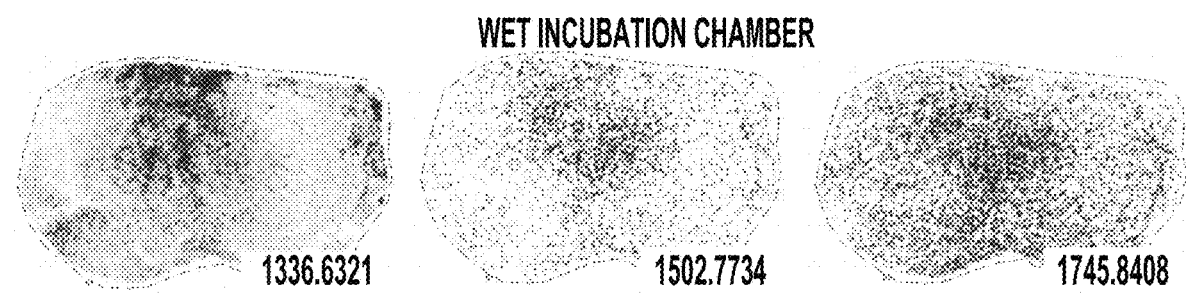

FIG. 10 compares peptide localization between the two experiments. Dry incubation showed nice localization for tryptic fragments corresponding to myelin basic protein. Ion images were also plotted for experiments with wet incubation chamber at the same m/z. Wet incubation showed no discernible localization. Thus, while wet incubation shows higher quality spectrum it causes extensive delocalization and is not recommended.

FTICR Imaging of Coronal Section of Rat Brain

Figure 11:
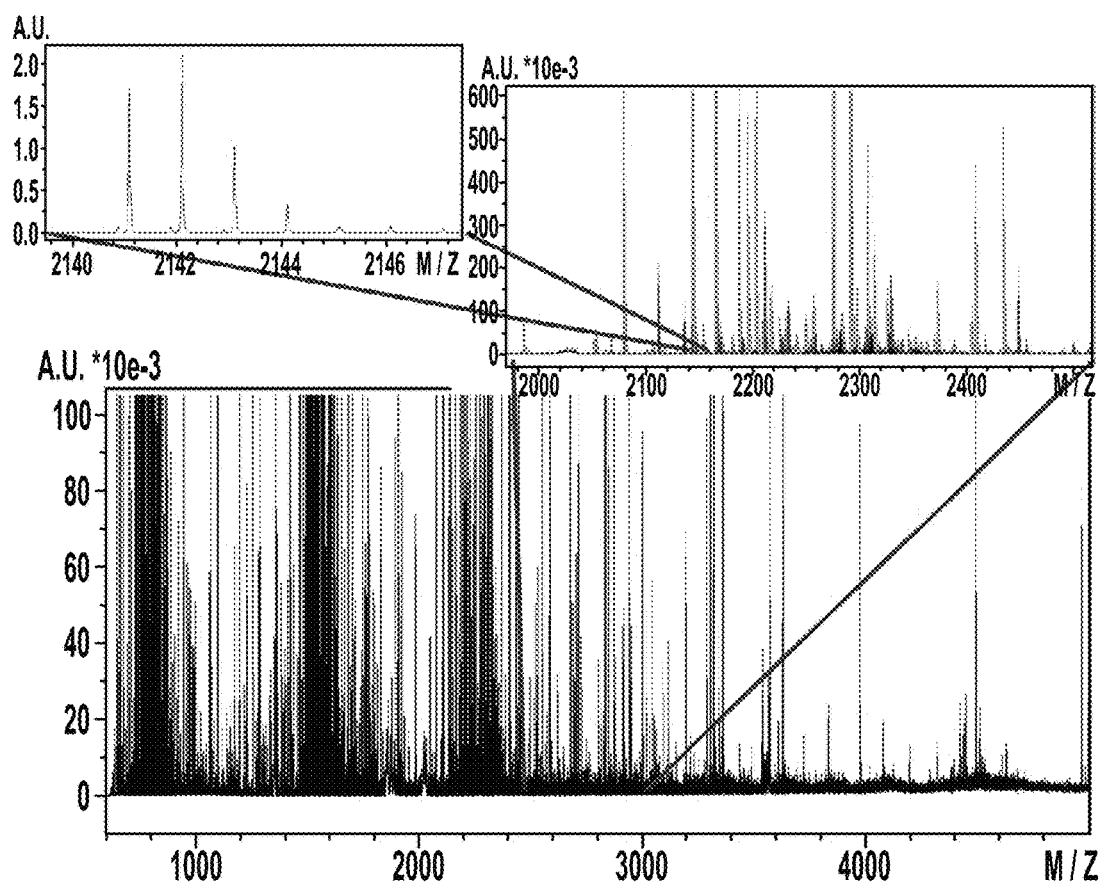
FIG. 11 provides mass spectrometry images giving a representative spectrum acquired from rat brain tissue section using pre-coated slides. The tissue thickness was 4 µm. Digestion was conducted for 4 h at 37° C. While the spectrum shows hundreds of signals, the insets demonstrate these signals highly resolvable.

Once the feasibility of the digestion in the ionic matrix was established, and the optimal trypsin and matrix densities were determined, the usefulness of these pre-coated substrates for MALDI IMS was demonstrated using rat brain tissue. The rat brain tissue section was cut at 4 μm and prepared using the procedure described in FIG. 3. The digestion was conducted for 4 h at 37° C. Analysis by MALDI FTICR generated hundreds of signals in 1000-5000 m/z range as shown in FIG. 11. The mass resolution was 130,000 at m/z of 1000. Many of the detected signals were matched to tryptic fragments of the proteins found in rat brain using LC-MS/MS analysis.

Myelin basic protein, essential in the formation of central nervous system and neuronal transmission, was identified using this method. Boggs, J. M., Cell Mol. Life Sci. 63, 1945-1961 (2006). The major isoform in adult rat brains has been reported to have a molecular weight of 14.2 kDa. Theoretical tryptic peptides of 14.2 kDa isoform of myelin basic protein were generated in mMass software. Comparison of the experimental peaks in the average spectrum with the calculated masses yielded 13 matches within 1 ppm. Ion images corresponding to all of those peaks show co-localization providing further verification in the identification. Selected images are shown in FIG. 12. These images indicate that the myelin basic protein is localized in corpus callosum and thalamus. A similar distribution was observed in the previous study. Groseclose, M. R. et al., J. Mass Spectrom. 42, 254-262 (2007).

PEP-19 and neurogranin were also identified using a similar procedure of mass matching. FIG. 13 shows that neurogranin is localized in the cerebral cortex and hippocampal region. PEP-19 is localized with high intensity in the thalamus and with reduced intensity in the cerebral cortex. These distributions are in agreement with the previous study. Seeley, E. H. and Caprioli, R. M., P.N.A.S. 105, 18126-18131 (2008). Table 3 includes the data for these three proteins, and includes the molecular weight of intact protein (MW), the MW for observed tryptic peptides, and the sequence determined using accurate mass matching. The highest error observed in any of these matches was 1.3 ppm suggesting a high level of confidence in our identifications.

TABLE 1

List of proteins detected in a coronal rat brain section.

| Protein detected in the tissue | Tryptic peptides from In Situ Digest | | | |
|---|---|---|---|---|
| | $[M + H]^+_{exp}$ | $[M + H]^+_{cal}$ | ppm | Sequence |
| Myelin Basic Protein (14.2 kDa) | 861.4358 | 861.4360 | -0.2 | r.SGSPMARR. |
| | 1019.5651 | 1019.5646 | 0.5 | r.HGFLPRHR.d |
| | 1067.5023 | 1067.5017 | 0.6 | r.FSWGGRDSR.s |
| | 1336.6318 | 1336.6314 | 0.3 | k.YLATASTMDHAR.h |
| | 1460.7168 | 1460.7169 | -0.1 | r.TQDENPVVHFFK.n |
| | 1502.7709 | 1502.7710 | -0.1 | r.TTHYGSLPQKSQR.t |
| | 1745.8385 | 1745.8388 | -0.1 | r.HGSKYLATASTMDHAR.h |
| | 1755.8643 | 1755.8660 | -1.0 | r.DTGILDSIGRFFSGDR.g |
| | 2141.1123 | 2141.1138 | -0.7 | r.TQDENPVVHFEKNIVTPR.t |
| Neurogranin (7.5 kDa) | 1064.5233 | 1064.5232 | 0.1 | k.GPGPGGPGGAGGAR.g |
| | 1192.6200 | 1192.6181 | 1.5 | r.KGPGPGGPGGAGGAR.g |
| PEP-19 (6.8 kDa) | 1923.8266 | 1923.8277 | -0.6 | k.VQEEFDIDMDAPETER.a |
| | 2051.9231 | 2051.9226 | 0.2 | k.KVQEEFDIDMDAPETER.a |

FTICR Imaging of Horizontal Section of Rat Brain

A horizontal rat brain section was also prepared using the pre-coated approach. FIG. 10 shows the obtained ion images. Image data were collected at a spatial resolution of 100 μm (pixel spacing) with ~16,000 pixels. The results are shown in FIG. 14. The peptides are listed in Table 4, including molecular weight of intact protein (MW), the MW for observed tryptic peptides, and the sequence determined using accurate mass matching. Even at this modest resolution, substructures within the brain (white matter and molecular layer) are clearly resolved. To minimize interferences from overlapping isotopic patterns, images were plotted by selecting only the highest intensity isotope for each peptide. All peptides corresponding to the same protein show co-localization. Myelin basic protein was localized in the corpus callosum and the white matter in the cerebellum region. Neurogranin is present in the cerebral cortex and absent from the cerebellum region. Brain acid soluble protein 1 was localized fairly uniformly in the brain except for cerebellum region. Myristoylated alanine-rich C-kinase substrate was present in high concentration in the molecular layer and in lower concentration in the cerebral cortex and the thalamus. It was absent from the white matter and the corpus callosum.

Example 2

Imaging Lipids Using the Pre-Coated Slides

In a typical post-coated preparation for protein or peptide analysis, organic washes are typically used to remove lipids. Seeley, E. H. et al., J. Am. Soc. Mass Spectr. 19, 1069-1077 (2008). After these organic washes, lipids signals in the mass

TABLE 1

List of proteins detected in a horizontal rat brain section.

Tryptic peptides from In Situ Digest

| Protein detected in the tissue | $[M + H]^+_{exp}$ | $[M + H]^+_{cal}$ | ppm | Sequence |
| --- | --- | --- | --- | --- |
| Myelin Basic Protein (21.5 kDa) | 1081.5472 | 1081.5425 | 4.4 | r.FFSGDRGAPK.r |
|  | 1502.7742 | 1502.7710 | 2.1 | r.TTHYGSLPQKSQR.t |
|  | 1745.8407 | 1745.8388 | 1.1 | r.HGSKYLATASTMDHAR.h |
|  | 2141.1096 | 2141.1138 | -2.0 | r.TQDENPVVHFEKNIVTPR.t |
|  | 2933.5194 | 2933.5268 | -2.5 | r.TQDENPVVHFFKNIVTPRTPPPSQGK.g |
| Neurogranin (7.5 kDa) | 1192.6125 | 1192.6181 | -4.7 | r.KGPGPGGPGGAGGAR.g |
|  | 1781.8427 | 1781.8460 | -1.9 | k.SGECGRKGPGPGGPGGAGGAR.g |
|  | 1904.8947 | 1904.8958 | -0.6 | r.KGPGPGGPGGAGGARGGAGGGPSGD. |
| Brain Acid Soluble Protein 1 (21.8 kDa) | 2132.9216 | 2132.9214 | 0.1 | k.AGEASAESTGAADGAPQEEGEAK.k |
|  | 2673.3394 | 2673.3366 | 1.1 | k.APAPAAPAAEPQAEAPVASSEQSVAVKE. |
|  | 3011.3897 | 3011.3865 | 1.1 | k.SEGAAEEQPEPAPAPEQEAAAPGPAAGGEAPK.a |
|  | 3283.5230 | 3283.5197 | 1.0 | k.AGEASAESTGAADGAPQEEGEAKKTEAPAAGPEAK.s |
|  | 3565.6542 | 3565.6565 | -0.6 | k.AEPEKSEGAAEEQPEPAPAPEQEAAAPGPAAGGEAPK.a |
| Myristoylated Alanine-rich C-Kinase Substrate (29.8 kDa) | 2432.0937 | 2432.0848 | 3.6 | r.EAEAAEPEQPEQPEQPAAEEPR.a |
|  | 2799.2164 | 2799.2048 | 4.1 | k.DEAAAAAGGDAAAAPGEQAGGAGAEGAEGGESR.e |
|  | 3558.6081 | 3558.5991 | 2.6 | r.EAEAAEPEQPEQPEQPAAEEPRAEEPSEAVGEK.a |
| Spectrin Alpha Chain, Non-oythrocytic 1 (284 kDa) | 1676.7818 | 1676.7762 | 3.3 | k.HEDFEKSLSAQEEK.i |
|  | 1774.8493 | 1774.8541 | -2.7 | k.LIQNNHYAMEDVATR.r |
|  | 2271.1482 | 2271.1490 | -0.3 | k.HQKHQAFEAELHANADRIR.g |

CONCLUSIONS

Matrix and trypsin pre-coated slides provide a simple approach to image proteins and lipids within biological tissues. The pre-coated method reduces the burden of sample preparation from the end user and allows faster sample preparation. The pre-coated slides could be stored in a freezer and can be used to prepare multiple tissue samples at the same time. The tissues are simply mounted on the pre-coated substrate, hydrated and then incubated in the oven.

The molecular information can be identified by linking MALDI imaging data to LC-MS/MS using accurate mass. The co-localization of peptides coming from the same parent protein provides additional verification in the identification. Some large proteins were identified using MALDI-IMS including myristoylated alanine-rich C-kinase substrate (29.8 kDa) and spectrin alpha chain, non-erythrocytic 1 (284 kDa).

One challenge to the pre-coated methodology is that the tissue section cannot be washed after mounting onto the pre-coated slides as that might dissolve the trypsin and matrix coating. Thus, peptide sensitivity is reduced due to the presence of lipids. The advantage here is that lipids can also be imaged in addition to peptides on the same tissue section. Future approaches may investigate washing lipids from the tissue immediately after extraction from the animal and before freezing.

spectrum are greatly reduced. Since no organic washes are utilized in the pre-coated approach, lipid signals can also be detected along with the peptides. FIG. 15 shows selected ion images for major lipids found in rat brain. Tentative identifications based on mass accuracy are also listed. These lipids have been previously identified in our lab.

Example 3

Storage Conditions for Slides

A second major challenge in the development of improved methods of IMS was the inability to store pre-coated slides at 4° C. due to reduced performance after storage for 6 to 18 months. The storage ability was investigated in more detail by using an assay to measure the trypsin activity on the pre-coated surface. Standard substrates such as p-nitroaniline or nα-benzoyl-DL-arginine 4-nitroanilide hydrochloride could be used to measure trypsin activity after it is deposited on the surface. Erlanger, B. F. et al., Arch. Biochem. Biophys. 95, 271-278 (1961).

Figure 16:
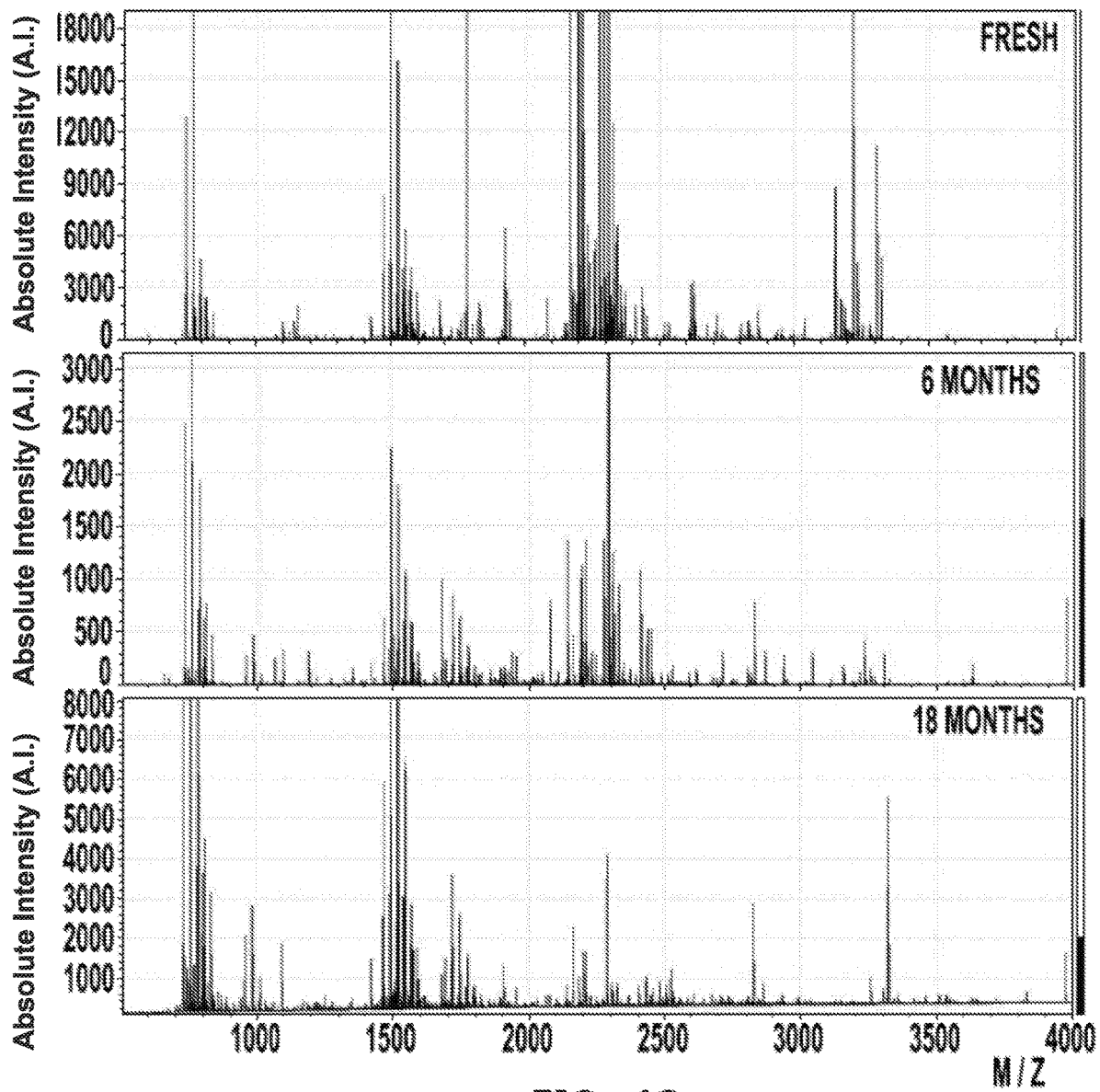
FIG. 16 provides a representative mass spectra acquired from serial rat brain tissue sections using a freshly prepared pre-coated slide, a 6-month-old slide, and a 8-month-old slide. Serial rat brain tissue sections were mounted on the pre-coated slides and incubated overnight at 37° C. The relative amount of lipid and peptide signal are compared to evaluate the overall performance. Lipid signals are located at m/z 600-750 and 1450-1600. Peptide signals appear between m/z 1600-4000, although some peptides signals are interspersed with the lipid signals. The relative amount of peptide signal is higher from freshly prepared slides and lower for 6- and 18-month-old slides.

Ideally, trypsin pre-coated slides would be prepared in batches and used as needed. Thus, it is important to establish the performance of trypsin pre-coated slides after storage. The slides were stored at 4° C. for 6 months and 18 months, and their performance was compared with a freshly prepared slide. In all three cases, standard preparation protocol was employed including 4 μm tissue thickness, 5 min hydration, incubation at 37° C. overnight (~16 h) and 10% TFA rinse. FIG. 16 compares the mass spectra generated from each of the three slides using serial rat brain tissue sections. Since the data for these slides was acquired separately, the absolute ion intensity is not directly comparable. However, relative ion intensity can be compared by examining the peptide signals between m/z 1700-4000 and the broad lipid peaks around m/z 800 and 1500. In the case of freshly prepared slides, the peptide signal was relatively strong between 1700-4000. For 6- and 18-month-old slides, the signal was dominated by lipid peaks although some peptides were seen. Thus, we conclude that the performance of the stored slides was reduced after storage.

FIG. 17 compares the ion images obtained from the three slides. Most abundant tryptic fragments of myelin basic protein from each experiment are chosen. Freshly prepared slides performed the best with crisp ion images and clear spatial localization, especially in the cerebellum region. For 6- and 18-month-old slides, the quality of the ion images deteriorated in two aspects. First, the ion images were noisier for older slides. Secondly, the finger-like structures in the cerebellum region were poorly defined.

Table 5 compares the signal-to-noise (S/N) ratio for the three data sets of tryptic fragments of myelin basic protein. The inventors found that the S/N ratio was between 200 and 700 for a freshly prepared slide. For a 6-month slides, the S/N ratio is below 100 except for the m/z of 2141.109. For a 18-month-slide, the S/N ratio was even lower ranging between 10-70.

TABLE 1

Comparison of signal-to-noise ratio for three sets of slides
Myelin Basic Protein

| m/z | S/N, Fresh | m/z | S/N, 6 months | m/z | S/N, 18 months |
|---|---|---|---|---|---|
| 1081.548 | 280.3 | 1019.567 | 31.9 | 861.436 | 61.2 |
| 1502.771 | 589.4 | 1336.625 | 34.3 | 1013.590 | 13.3 |
| 1745.839 | 249.2 | 2141.109 | 575.0 | 1502.771 | 33.8 |
| 2141.112 | 703.9 | 2370.187 | 79.4 | 1745.839 | 15.6 |
| 2933.516 | 205.8 | 2453.229 | 19.6 | 2141.112 | 25.9 |

Example 3

Development of Microarrays to Minimize Analyte Delocalization

Figures 17A, 17B, 17C, 18:
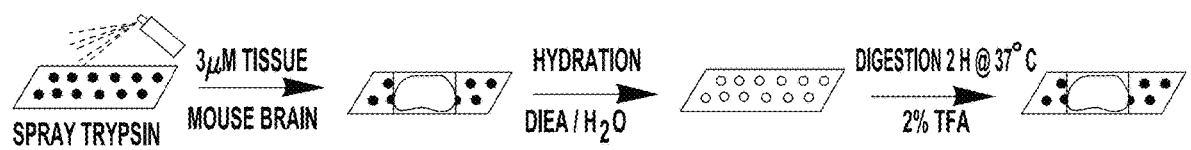
FIGS. 17A-17C provide ion images of myelin basic protein acquired using freshly prepared pre-coated slides with those obtained using slides stored for 6 months and 18 months. Serial rat brain tissue sections were mounted onto the pre-coated slides and incubated overnight at 37° C. Ion images corresponding to tryptic fragments of myelin basic protein are shown. Freshly prepared slides show higher quality images and the finger-like structures in the cerebellum regions are fully resolved. Older slides show noisier images and the finger-like structures are poorly resolved.
FIG. 18 provides a schematic representation of the workflow for on-tissue digestion and peptide imaging.
Figure 19:
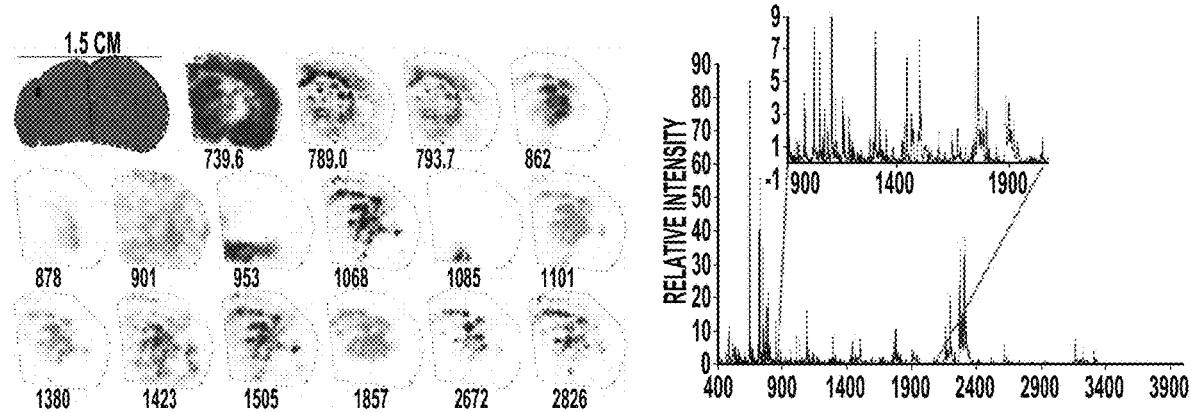
FIG. 19 provides images and a graph showing the images peptides of a coronal section of rat brain using a pre-coated array containing both matrix and trypsin. The right half of the tissue section was imaged. A representative mass spectrometry spectrum is shown on the right.

As discussed in Example 1, hydration of the tissue can induce analyte delocalization causing a loss in spatial information of biomolecules. Matrix microarrays have been fabricated using the lithographic procedures to minimize delocalization of analytes. FIG. 18 illustrates the employed workflow using arrayed targets. Trypsin was manually sprayed onto the matrix array, and thin tissue sections (3-5 µm) were thaw-mounted on this slide. After the tissue was mounted, the slide was placed in a chamber saturated with DIEA and water for 2 min. The acidic matrix absorbed the amine forming an ionic matrix. After digestion for 2 h at 37° C., the slide is rinsed with 2% TFA to remove the DIEA and recast the matrix as crystals.

After the rinsing step, the sample was ready to be analyzed using mass spectrometry. Using this approach, we imaged the coronal section of the rat brain using a Bruker Daltonics Autoflex Speed MALDI-TOF. FIG. 17 shows the obtained imaging results. Ion images corresponding m/z of 789.0 and 793.7 show high intensity in the corpus callosum region whereas ion images corresponding m/z of 862 and 1857 show localization in the thalamus.

Figure 20:
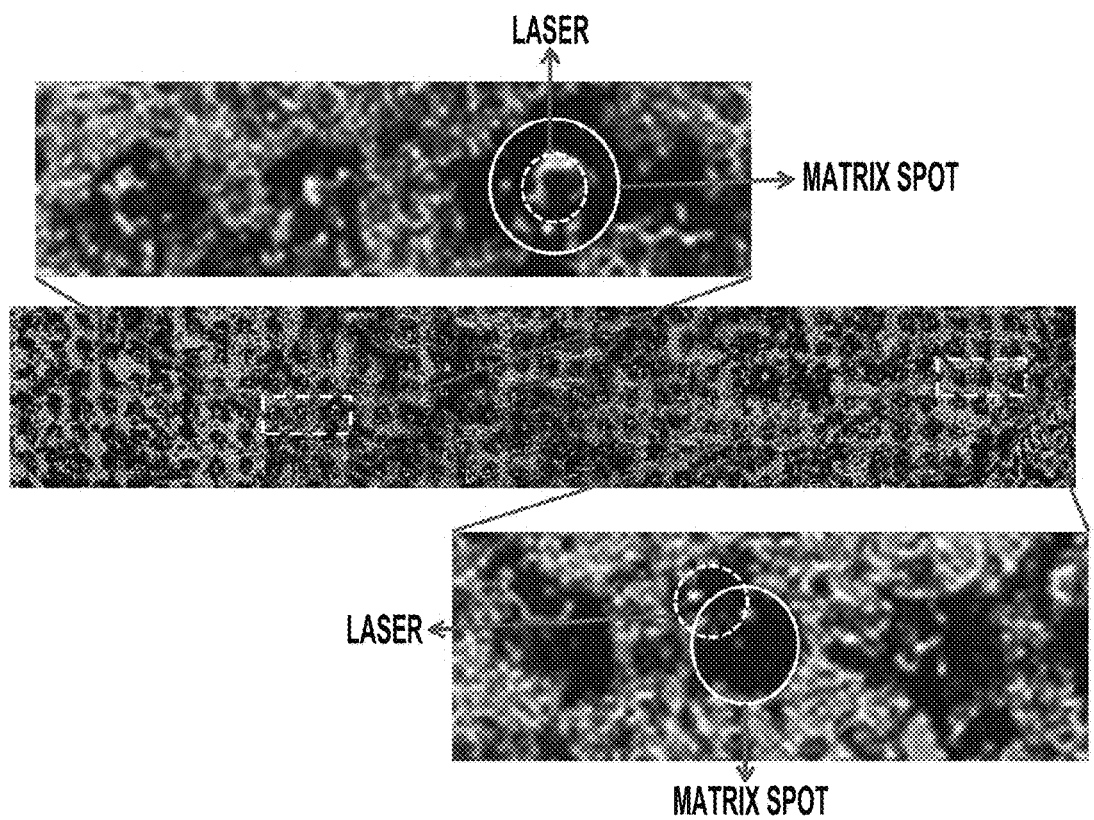
FIG. 20 provides images illustrating the challenge of aligning the laser with the matrix array. The middle figure shows the optimal image of the arrayed target after MALDI analysis. The laser ablation craters are superimposed on top of the matrix spots. While the top inset indicates where the laser spot is aligned with the matrix spot, the bottom inset indicates where ablation craters and matrix spots are misaligned.

Microarray technology requires alignment of the laser with the matrix spots. FIG. 20 illustrates this problem. The middle figure shows the optical image of the target after laser interrogation. The top zoomed-in inset indicates that the laser ablation crater is aligned with the matrix spot generating an optimal signal. However, the lower inset indicates that laser ablation was at the edge of matrix spot generating a non-optimal signal. At 100 µm pitch distance, rotational and translational alignment of the laser with matrix spots becomes challenging. Presently, the FlexImaging software only allows for step size adjustment in increments of 1 µm and does not allow for rotational adjustment which is dictated by teaching points. Thus, for this approach to work modifications need to be made to the software acquisition system Example 4

Application of Pre-Coated Slides to Formalin-Fixed Paraffin-Embedded Tissues

Formalin-fixed paraffin embedded (FFPE) tissues are tremendously important in the clinical environment given the vast repositories of such samples in tissue banks with associated pathological, clinical, and patient outcome information. Groseclose, M. R. et al., Proteomics 8, 3715-3724 (2008); De Sio, G. et al., Mol. Biosyst. 11, 1507-1514 (2015); Maes, E. et al., Amino Acids 45, 205-218 (2013). Multiple groups have developed methods imaging FFPE tissues by IMS that involve laborious antigen retrieval and on-tissue digestion methods. Havlis, J. et al., Anal. Chem. 75, 1300-1306 (2003); De Sio, G. et al., Mol Biosyst. 11, 1507-1514 (2015); Casadonte, R. et al., Nat. Protoc. 6, 1695-1709 (2011); Lemaire, R. et al., J. Proteome Res. 6, 1295-1305 (2007). The application of enzyme and matrix pre-coated slides can be particularly useful for FFPE tissues.

Figure 21:
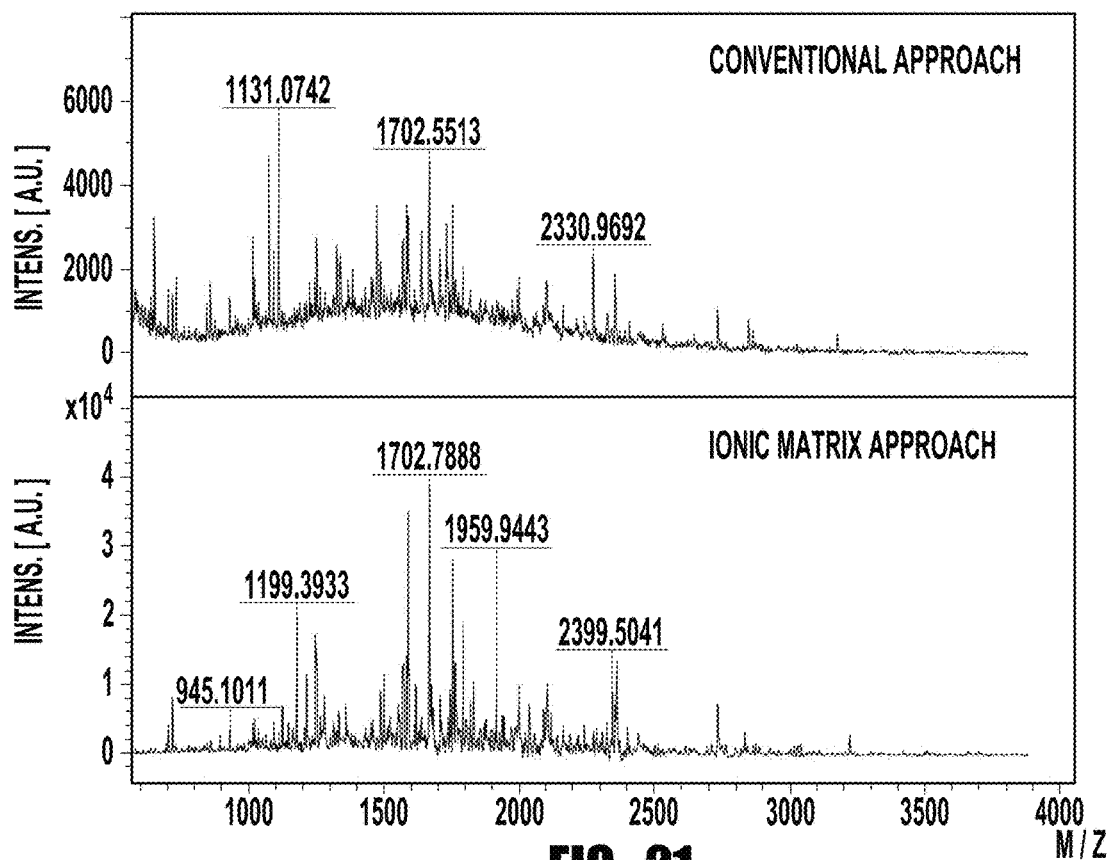
FIG. 21 provides two graphs showing digestion of formalin-fixed paraffin-embedded (FFPE) rat brain tissue by hand-spotting trypsin in the ionic matrix and trypsin in 100 mM ammonium bicarbonate buffer solution on serial tissue sections. The trypsin concentration was the same in both cases, and the same region of the tissue was used.

In a proof-of-principle experiment, the ability of the ionic matrix to enable digestion of FFPE tissues was tested. The FFPE rat brain tissue underwent typical processing conditions including sectioning, mounting on an ITO-coated glass substrate, paraffin removal, and antigen retrieval. After these processing steps trypsin in ionic matrix was spotted on top of the tissue to digest the proteins. A serial tissue section was prepared using the conventional approach using trypsin in ammonium buffer solution. FIG. 21 below compares the mass spectral results. Several peaks were observed in both cases showing efficient digestion. Ionic matrix preparation provided richer spectra with more peaks and higher intensities.

Figure 22:
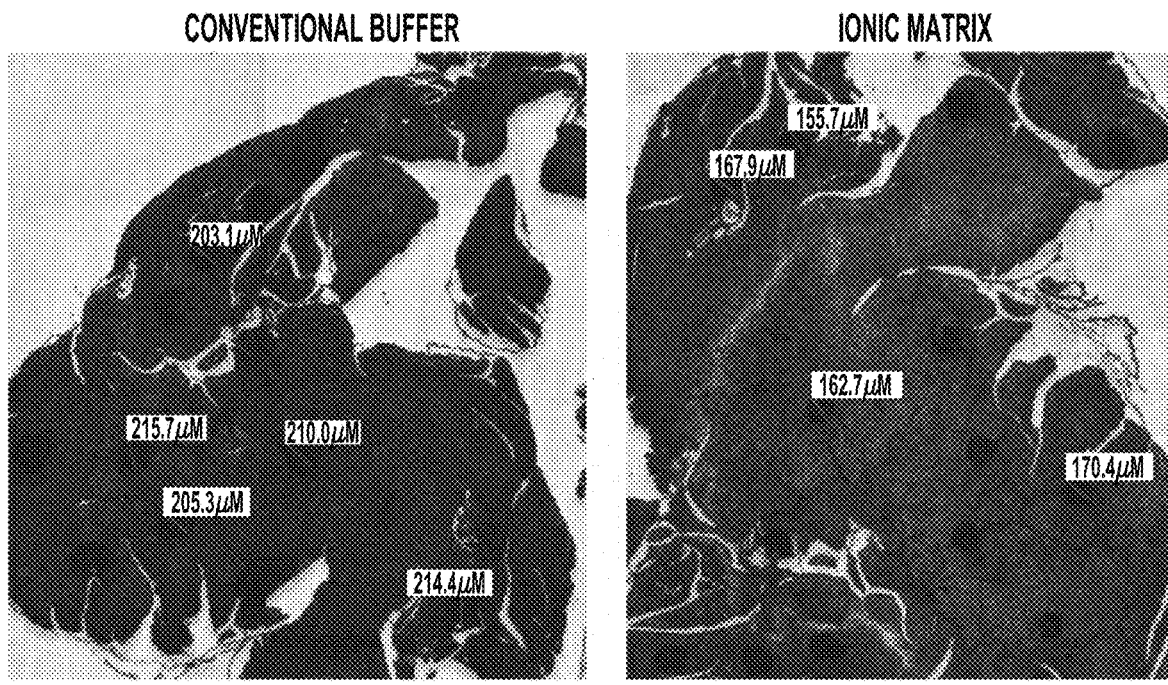
FIG. 22 provides images comparing the spot sizes using a conventional buffer approach and the ionic matrix approach.

An additional advantage of the ionic matrix preparation is that smaller spot sizes were obtained due to a higher surface tension and a single step deposition. FIG. 22 shows the spot sizes as measured after robotic deposition. The average spot diameter for a preparation involving buffer solution was 210 µm compared to 164 µm using ionic matrix approach. This reduction in spot size will be especially beneficial for histology directed analysis where the area of analysis is directly limited by the spot size.

Figure 23:
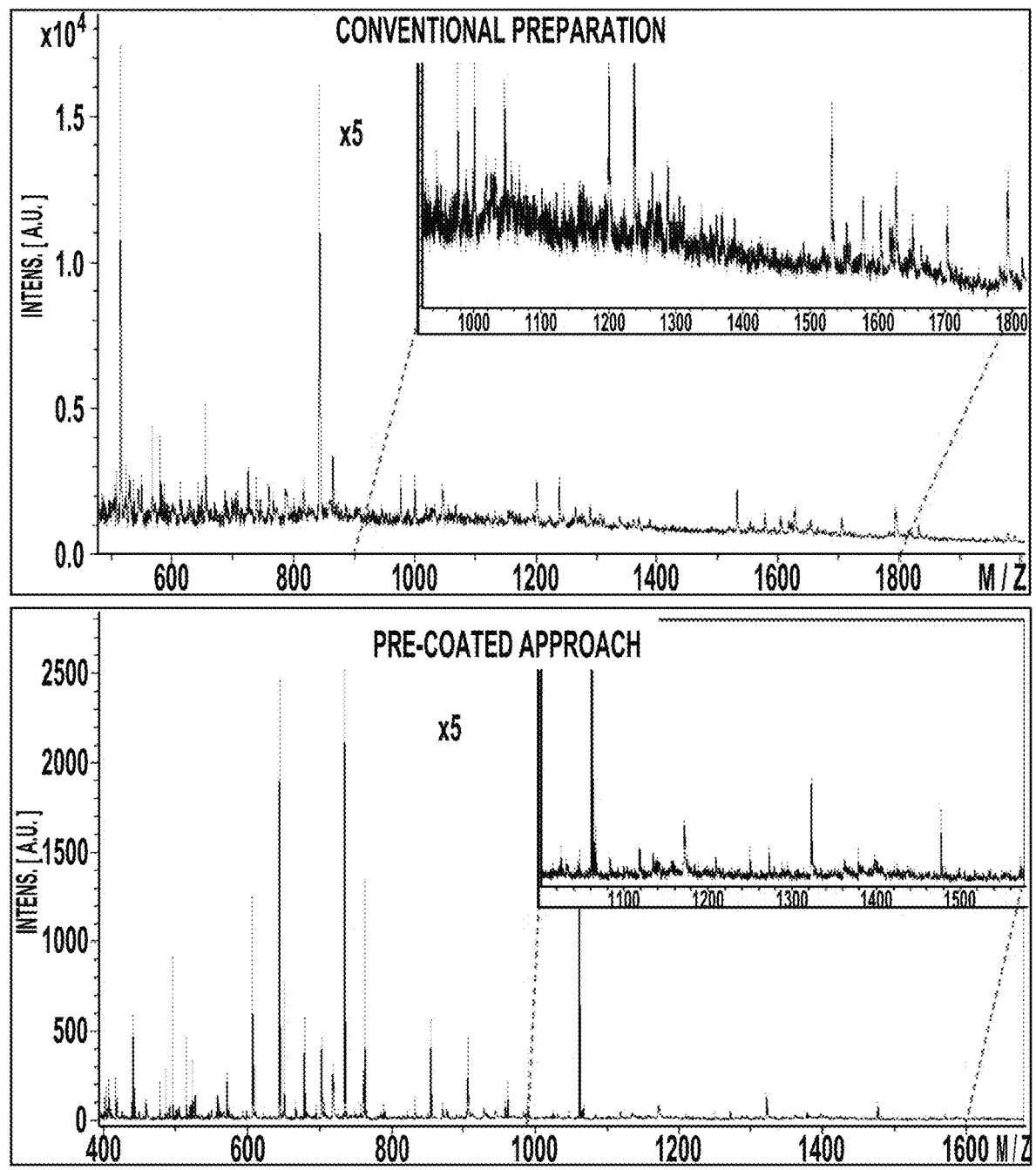
FIG. 23 provides representative spectra obtained using MALDI-TOF/TOF from digestion of FFPE rat brain tissue using the conventional approach employing a robotic spotter and the pre-coated approach.

Lastly, the applicability of pre-coated slides towards analysis of FFPE tissues was evaluated for an imaging experiment. Sagittal mouse brain tissue sections were prepared using conventional robotic spotting methods and the pre-coated methods. FIG. 23 compares the representative mass spectra obtained from these two experiments. Pre-coated slides showed better signal-to-noise ratio suggesting improved digestion although these peaks need to be identified to make conclusive statements.

Figure 24:
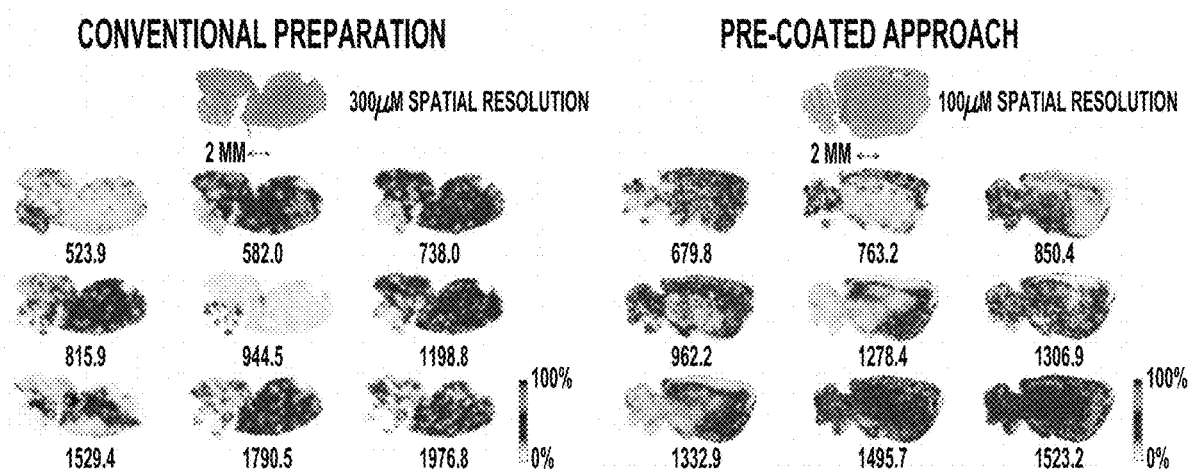
FIG. 24 provides images displaying a digestion of FFPE rat brain tissue by trypsin in the ionic matrix and trypsin in 100 mM ammonium bicarbonate buffer solution. A 1 uL solution was hand-spotted onto serial tissue sections. The trypsin concentration was the same in both cases (0.1 mg/mL).

The ionic matrix/trypsin solution is also effective for the digestion of proteins in FFPE tissue. FFPE mouse kidney was sectioned at 6 μm and mounted on conductive slides. Paraffin was removed with a series of xylenes and graded ethanol washes. Antigen retrieval was performed by pressure-heating the sections in TRIS buffer. Trypsin was acoustically spotted onto the surface in a mixture of CHCA matrix, trypsin and N,N-diisopropylethylamine to create an ionic matrix. Trypsin in an ionic matrix acoustically spotted onto FFPE tissue is capable of enzymatic digestion similar to that obtained by traditional on-tissue digestion methods (spotting trypsin in buffer, allowing incubation, and subsequently spotting CHCA matrix). These data support the strategy of delivering trypsin in an ionic matrix mixture to produce successful enzymatic digestion. A pre-coated matrix/trypsin slide will significantly reduce the number of sample preparation steps required by the end user in a post-coating approach, which saves time and makes the technology more feasible for clinical diagnostic settings FIG. 24 compares the ion images acquired using the conventional methods and the pre-coated approach. Due to different extraction medium, a different selection of ions was observed in each case. A step size of 300 μm was used in the case of conventional preparation. For the pre-coated approach, a step size of 100 μm was used allowing observation finer biological detail. These experiments show the promise of pre-coated slides in preparing clinically significant FFPE samples.

Example 5

Protocols for the Analysis of FFPE Tissue by Imaging Mass Spectrometry

The pre-coated targets will be tested for their ability to digest both fresh frozen and fixed tissue. Fixed tissue presents a series of analytical difficulties because proteins are typically cross-linked and tissue is embedded in a paraffin substrate. In proteomic work-flows for the analysis of FFPE tissues, paraffin is removed using a series of xylene and ethanol washes and the cross-linked proteins are denatured using pressure and heat, termed antigen retrieval, to aid enzymatic digestion. The inventors will develop paraffin removal protocols and antigen retrieval steps that are compatible with the matrix/enzyme coating. Commercially available protein denaturing systems (e.g., Denator Stabilizor system) to aid rapid antigen retrieval on a pre-coated surface without disturbing the matrix coating will be tested.

As tissue is successfully applied to the matrix/enzyme pre-coated slides, the inventors will evaluate the sample preparation via MS profiling and imaging experiments as well as LC-MS/MS. In addition, the pre-coated targets will be imaged at increasingly higher spatial resolutions to determine resolution limits of the method. Three different tissue types will be utilized throughout method development. First, tissue that is fixed by non-crosslinking methods (e.g., ethanol fixation, PAXgene, etc.) and is paraffin-embedded will be prepared. This tissue type will allow optimization of paraffin removal methods. Second, tissue that is formalin-fixed and re-frozen (without paraffin embedding) will be used to optimize digestion of fixed tissue without paraffin interference. Finally, the FFPE tissues will be used. In order to assess resolution of tissue features, test tissues will be selected containing morphological targets of at least 25 microns. Target peptides of interest will be identified from specific areas by leveraging hydrogel technologies with subsequent LC-MS/MS analysis. The in situ tryptic fragments extracted from the tissue surface will be compared to that taken from serial sections and to digested peptides from bulk protein extractions of the same tissue to evaluate the efficiency of digestion and protein recovery.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for analyzing animal tissue, comprising the following steps in sequential order:
    a) first, applying a matrix suitable for use with mass spectrometry to an analysis substrate to form a matrix surface on the analysis substrate;
    b) second, adding a protease to the matrix surface to form a pre-coated analysis substrate;
    c) third, placing, after steps a) and b), an animal tissue specimen on the pre-coated analysis substrate;
    d) fourth, allowing the protease to digest the animal tissue specimen on the analysis substrate; and
    e) fifth, analyzing the partially digested animal tissue specimen on the analysis substrate by mass spectrometer.

2. The method of claim 1, wherein the digested animal tissue specimen is analyzed for peptide content.

3. The method of claim 2, wherein the peptides are extracted from the animal tissue specimen using solvent extraction prior to analyzing the digested animal tissue specimen by mass spectrometry.

4. The method of claim 1, wherein the digested animal tissue specimen is analyzed for lipid content.

5. The method of claim 1, wherein the mass spectrometry is MALDI mass spectrometry.

6. The method of claim 1, wherein the protease is trypsin.

7. The method of claim 1, wherein the matrix comprises α-cyano-4-hydroxycinnamic acid.

8. The method of claim 1, wherein the substrate is a glass slide.

9. The method of claim 1, wherein the animal tissue specimen is formalin-fixed paraffin-embedded tissue.

10. The method of claim 1, wherein the matrix is formed as a microarray.

11. The method of claim 1, further comprising imaging the digested animal tissue specimen that has been analyzed.

12. The method of claim 1, wherein the animal tissue specimen is hydrated before partial digestion, and the matrix is crystallized after partial digestion.

13. The method of claim 1, wherein the matrix has a density from 0.3 to 3.0 mg/cm$^2$.

14. The method of claim 1, wherein the protease is present at a concentration from about 1 to 10 μg/cm$^2$.

15. A method for analyzing animal tissue using a pre-coated analysis substrate, comprising the following steps in sequential order:
    a) first, placing an animal tissue specimen on an analysis substrate pre-coated with both a matrix suitable for use with mass spectrometry and a protease;
    b) second, allowing the protease to partially digest the animal tissue specimen on the analysis substrate; and
    c) third, analyzing the digested animal tissue specimen on the analysis substrate by mass spectrometry.

16. The method of claim 15, wherein the pre-coated analysis substrate has been stored for 24 hours or more before an animal tissue specimen is placed on the pre-coated analysis substrate.

17. A method for analyzing animal tissue, comprising the following steps in sequential order:
 a) first coating a protease on a surface of an analysis substrate to form a protease coated analysis substrate;
 b) second, placing, after step a), an animal tissue specimen on the protease coated analysis substrate;
 c) third, allowing the protease to digest the animal tissue specimen on the analysis substrate; and
 d) fourth, analyzing the digested animal tissue specimen on the analysis substrate by mass spectrometry.

18. The method of claim 17, wherein the digested animal tissue specimen is analyzed for peptide content.

19. The method of claim 17, wherein the digested animal tissue is coated with a matrix suitable for use with mass spectrometry before analysis.

20. A method of preparing a pre-coated analysis substrate, comprising:
 a) forming a matrix surface on an analysis substrate;
 b) adding a protease to the matrix surface to form a pre-coated analysis substrate; and
 c) storing the pre-coated analysis substrate for 24 hours or more before use.

21. The method of claim 20, wherein the protease is trypsin.

22. The method of claim 20, wherein the matrix comprises α-cyano-4-hydroxycinnamic acid.

23. The method of claim 20, wherein the matrix is formed as a microarray.

24. The method of claim 20, wherein the pre-coated substrate is stored for 1 month or more.

25. The method of claim 20, wherein the analysis substrate is a glass slide.

26. A pre-coated analysis substrate, prepared according to the method of claim 20.

* * * * *